US009522277B2

(12) United States Patent
Gunderson

(10) Patent No.: US 9,522,277 B2
(45) Date of Patent: Dec. 20, 2016

(54) LEAD INTEGRITY TESTING TRIGGERED BY SENSED SIGNAL SATURATION

(75) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 2575 days.

(21) Appl. No.: 12/180,911

(22) Filed: Jul. 28, 2008

(65) Prior Publication Data

US 2010/0023084 A1 Jan. 28, 2010

(51) Int. Cl.
*A61N 1/37* (2006.01)
*A61N 1/08* (2006.01)

(52) U.S. Cl.
CPC ........... *A61N 1/3706* (2013.01); *A61N 1/3702* (2013.01); *A61N 2001/083* (2013.01)

(58) Field of Classification Search
USPC ..................................................... 607/27–28
See application file for complete search history.

(56) References Cited

U.S. PATENT DOCUMENTS

| | | |
|---|---|---|
| 4,140,131 A | 2/1979 | Dutcher et al. |
| 4,332,256 A | 6/1982 | Brownlee et al. |
| 4,374,382 A | 2/1983 | Markowitz |
| 4,428,378 A | 1/1984 | Anderson et al. |
| 4,549,548 A | 10/1985 | Wittkampf et al. |
| 4,825,869 A | 5/1989 | Sasmor et al. |
| 4,860,749 A | 8/1989 | Lehmann |
| 4,899,750 A | 2/1990 | Ekwall |
| 4,913,146 A | 4/1990 | DeCote, Jr. |
| 4,944,746 A | 7/1990 | Iwata et al. |
| 5,003,975 A | 4/1991 | Hafelfinger et al. |
| 5,107,833 A | 4/1992 | Barsness |
| 5,117,824 A | 6/1992 | Keimel et al. |
| 5,137,021 A | 8/1992 | Wayne et al. |
| 5,168,871 A | 12/1992 | Grevious |
| 5,184,614 A | 2/1993 | Collins et al. |
| 5,193,535 A | 3/1993 | Bardy et al. |
| 5,201,865 A | 4/1993 | Kuehn |

(Continued)

FOREIGN PATENT DOCUMENTS

| | | |
|---|---|---|
| WO | WO 97/36647 A1 | 10/1997 |
| WO | WO 02/18009 A1 | 3/2002 |

(Continued)

OTHER PUBLICATIONS

Reply to Written Opinion from corresponding PCT Application Serial No. PCT/US2008/009119 filed Apr. 22, 2010 (14 pages).

(Continued)

*Primary Examiner* — Eric D. Bertram

(57) ABSTRACT

Techniques for performing a lead integrity test in response to, e.g., during or after saturation of a sensed signal, e.g., a cardiac electrogram (EGM) signal, are described. A lead integrity test may comprise one or more impedance measurements for one or more leads. Possible causes of saturation of a sensed signal include lead conductor or connector issues, or other lead related conditions. A lead integrity test triggered in response to the saturation may be able to detect any lead related condition causing the saturation. A lead integrity test triggered in response to the saturation may advantageously be able to detect an intermittent lead related condition, due to the temporal proximity of the test to the saturation.

2 Claims, 10 Drawing Sheets

(56) References Cited

U.S. PATENT DOCUMENTS

| | | |
|---|---|---|
| 5,215,081 A | 6/1993 | Ostroff |
| 5,224,475 A | 7/1993 | Berg et al. |
| 5,226,415 A | 7/1993 | Girodo et al. |
| 5,292,343 A | 3/1994 | Blanchette et al. |
| 5,312,441 A | 5/1994 | Mader et al. |
| 5,314,450 A | 5/1994 | Thompson |
| 5,324,315 A | 6/1994 | Grevious |
| 5,354,319 A | 10/1994 | Wyborny et al. |
| 5,381,803 A | 1/1995 | Herleikson et al. |
| 5,383,909 A | 1/1995 | Keimel |
| 5,411,530 A | 5/1995 | Akhtar |
| 5,431,692 A | 7/1995 | Hansen et al. |
| 5,462,060 A | 10/1995 | Jacobson et al. |
| 5,507,746 A | 4/1996 | Lin |
| 5,507,786 A | 4/1996 | Morgan et al. |
| 5,534,018 A | 7/1996 | Wahlstrand et al. |
| 5,545,183 A | 8/1996 | Altman |
| 5,545,186 A | 8/1996 | Olson et al. |
| 5,549,646 A | 8/1996 | Katz et al. |
| 5,558,098 A | 9/1996 | Fain |
| 5,564,434 A | 10/1996 | Halperin et al. |
| 5,660,183 A | 8/1997 | Chiang et al. |
| 5,707,398 A | 1/1998 | Lu |
| 5,722,997 A | 3/1998 | Nedungadi et al. |
| 5,730,141 A | 3/1998 | Fain et al. |
| 5,741,311 A | 4/1998 | Mc Venes et al. |
| 5,755,735 A | 5/1998 | Richter et al. |
| 5,755,736 A | 5/1998 | Gillberg et al. |
| 5,755,742 A * | 5/1998 | Schuelke et al. .......... 607/27 |
| 5,776,168 A * | 7/1998 | Gunderson .......... 607/27 |
| 5,814,088 A | 9/1998 | Paul et al. |
| 5,868,793 A | 2/1999 | Nitzsche et al. |
| 5,891,170 A | 4/1999 | Nitzsche et al. |
| 5,891,179 A | 4/1999 | Er et al. |
| 5,897,577 A | 4/1999 | Cinbis et al. |
| 5,902,324 A | 5/1999 | Thompson et al. |
| 5,910,156 A | 6/1999 | Cinbis et al. |
| 5,944,746 A | 8/1999 | Kroll |
| 6,067,473 A | 5/2000 | Greeninger et al. |
| 6,070,097 A | 5/2000 | Kreger et al. |
| 6,085,118 A | 7/2000 | Hirschberg et al. |
| 6,112,119 A | 8/2000 | Schuelke et al. |
| 6,129,746 A | 10/2000 | Levine et al. |
| 6,141,585 A | 10/2000 | Prutchi et al. |
| 6,155,267 A | 12/2000 | Nelson |
| 6,169,923 B1 | 1/2001 | Kroll |
| 6,266,554 B1 | 7/2001 | Hsu et al. |
| 6,317,632 B1 | 11/2001 | Krig et al. |
| 6,317,633 B1 | 11/2001 | Jorgenson et al. |
| 6,434,428 B1 | 8/2002 | Sloman et al. |
| 6,445,952 B1 | 9/2002 | Manrodt et al. |
| 6,477,417 B1 | 11/2002 | Levine |
| 6,493,586 B1 | 12/2002 | Stahmann et al. |
| 6,629,931 B1 | 10/2003 | Begemann et al. |
| 6,650,931 B1 | 11/2003 | McClure et al. |
| 6,658,294 B1 | 12/2003 | Zadeh et al. |
| 6,721,600 B2 | 4/2004 | Jorgenson et al. |
| 6,760,624 B2 | 7/2004 | Anderson et al. |
| 6,788,971 B1 | 9/2004 | Sloman et al. |
| 6,865,141 B2 | 3/2005 | Tada et al. |
| 7,047,083 B2 | 5/2006 | Gunderson et al. |
| 7,167,747 B2 | 1/2007 | Gunderson et al. |
| 7,236,828 B2 | 6/2007 | Casavant et al. |
| 7,266,409 B2 | 9/2007 | Gunderson |
| 7,289,851 B2 | 10/2007 | Gunderson et al. |
| 7,333,855 B2 | 2/2008 | Gunderson et al. |
| 7,369,893 B2 | 5/2008 | Gunderson |
| 7,539,540 B2 | 5/2009 | Gunderson et al. |
| 7,567,835 B2 | 7/2009 | Gunderson et al. |
| 2001/0031997 A1 | 10/2001 | Lee |
| 2001/0037366 A1 | 11/2001 | Webb et al. |
| 2002/0091333 A1 | 7/2002 | Hsu et al. |
| 2002/0116031 A1 | 8/2002 | Vonk |
| 2002/0118215 A1 | 8/2002 | Ball et al. |
| 2002/0120307 A1 | 8/2002 | Jorgenson et al. |
| 2003/0074026 A1 | 4/2003 | Thompson et al. |
| 2003/0204215 A1 | 10/2003 | Gunderson et al. |
| 2004/0015197 A1 | 1/2004 | Gunderson |
| 2004/0088018 A1 | 5/2004 | Sawchuk et al. |
| 2004/0106955 A1 | 6/2004 | Swerdlow et al. |
| 2004/0122487 A1 | 6/2004 | Hatlestad et al. |
| 2004/0186388 A1 | 9/2004 | Gerasimov |
| 2004/0220631 A1 | 11/2004 | Burnes et al. |
| 2004/0230233 A1 | 11/2004 | Gunderson et al. |
| 2004/0230242 A1 | 11/2004 | van Dam et al. |
| 2005/0137636 A1 | 6/2005 | Gunderson et al. |
| 2005/0154421 A1 | 7/2005 | Ousdigian |
| 2005/0159785 A1 | 7/2005 | Rueter |
| 2006/0074454 A1 | 4/2006 | Freeberg |
| 2006/0235476 A1 | 10/2006 | Gunderson et al. |
| 2006/0264777 A1 | 11/2006 | Drew |
| 2008/0082012 A1 | 4/2008 | Gunderson et al. |
| 2008/0161872 A1 | 7/2008 | Gunderson |
| 2008/0300497 A1 * | 12/2008 | Krause et al. .......... 600/515 |

FOREIGN PATENT DOCUMENTS

| | | |
|---|---|---|
| WO | WO 03/077822 A2 | 9/2003 |
| WO | WO 2005/056109 A1 | 6/2005 |

OTHER PUBLICATIONS

International Search Report and Written Opinion from corresponding PCT Application Serial No. PCT/US2008/009119 mailed Apr. 27, 2009 (12 pages).

International Preliminary Report on Patentability from corresponding PCT Application Serial No. PCT/US2008/009119 dated Aug. 26, 2010 (9 pages).

\* cited by examiner

LEAD INTEGRITY TESTING TRIGGERED BY SENSED SIGNAL SATURATION

TECHNICAL FIELD

The disclosure relates to implantable medical devices, and, more particularly, to testing integrity of implantable medical device sensing components.

BACKGROUND

A variety of implantable medical devices for delivering a therapy and/or monitoring a physiological condition have been clinically implanted or proposed for clinical implantation in patients. Implantable medical devices may deliver electrical stimulation or fluid therapy and/or monitor conditions associated with the heart, muscle, nerve, brain, stomach or other organs or tissue. Some implantable medical devices may employ one or more elongated electrical leads carrying stimulation electrodes, sense electrodes, and/or other sensors. Implantable medical leads may be configured to allow electrodes or other sensors to be positioned at desired locations for delivery of stimulation or sensing. For example, electrodes or sensors may be carried at a distal portion of a lead. A proximal portion of the lead may be coupled to an implantable medical device housing, which may contain circuitry such as stimulation generation and/or sensing circuitry.

Implantable medical devices, such as cardiac pacemakers or implantable cardioverter-defibrillators, for example, provide therapeutic electrical stimulation to the heart via electrodes carried by one or more implantable leads. The electrical stimulation may include signals such as pulses or shocks for pacing, cardioversion or defibrillation. In some cases, an implantable medical device may sense intrinsic depolarizations of the heart, and control delivery of stimulation signals to the heart based on the sensed depolarizations. Upon detection of an abnormal rhythm, such as bradycardia, tachycardia or fibrillation, an appropriate electrical stimulation signal or signals may be delivered to restore or maintain a more normal rhythm. For example, in some cases, an implantable medical device may deliver pacing pulses to the heart of the patient upon detecting tachycardia or bradycardia, and deliver cardioversion or defibrillation shocks to the heart upon detecting tachycardia or fibrillation.

Leads associated with an implantable medical device typically include a lead body containing one or more elongated electrical conductors that extend through the lead body from a connector assembly provided at a proximal lead end to one or more electrodes located at the distal lead end or elsewhere along the length of the lead body. The conductors connect stimulation and/or sensing circuitry within an associated implantable medical device housing to respective electrodes or sensors. Some electrodes may be used for both stimulation and sensing. Each electrical conductor is typically electrically isolated from other electrical conductors and is encased within an outer sheath that electrically insulates the lead conductors from body tissue and fluids.

Cardiac lead bodies tend to be continuously flexed by the beating of the heart. Other stresses may be applied to the lead body during implantation or lead repositioning. Patient movement can cause the route traversed by the lead body to be constricted or otherwise altered, causing stresses on the lead body. Such stresses may lead to fracture of one or more conductors of the lead. Additionally, the electrical connection between implantable medical device connector elements and the lead connector elements can be intermittently or continuously disrupted. Connection mechanisms, such as set screws, may be insufficiently tightened at the time of implantation, followed by a gradual loosening of the connection. Also, lead pins may not be completely inserted. In some cases, changes in lead conductors or connections may result in intermittent or continuous changes in lead impedance.

Short circuits, open circuits or significant changes in impedance may be referred to, in general, as lead related conditions. In the case of cardiac leads, sensing of an intrinsic heart rhythm through a lead can be altered by lead related conditions. Structural modifications to leads, conductors or electrodes may alter sensing integrity. Furthermore, impedance changes in the stimulation path due to lead related conditions may affect sensing and stimulation integrity for pacing, cardioversion, or defibrillation. In addition to lead related conditions, conditions associated with sensor devices or sensing circuitry, as well as conditions associated with electrodes or sensors not located on leads, may affect sensing integrity.

SUMMARY

In general, this disclosure is directed to techniques for performing a lead integrity test in response to, e.g., during or after, saturation of a signal sensed via the lead. A lead integrity test may comprise one or more impedance measurements for one or more leads. The lead integrity test may be performed by an implantable medical device (IMD) coupled to leads. In some examples, the IMD is a cardiac pacemaker, cardioverter, defibrillator, or pacemaker-cardioverter-defibrillator, and the sensed signal is a cardiac electrogram (EGM) signal.

Possible causes of saturation of a sensed signal include lead conductor or connector issues (e.g., a conductor fracture), or other lead related conditions (e.g., an insulation breach). A lead integrity test triggered in response to the saturation may be able to detect any lead related condition causing the saturation. A lead integrity test triggered in response to the saturation may advantageously be able to detect an intermittent lead related condition, due to the temporal proximity of the test to the saturation.

In some examples, an IMD or other device detects saturation of the sensed signal by comparison of the sensed signal to a threshold. A saturated signal may be saturated at a high or low value, e.g., a positive or negative value, and, accordingly, the comparison may involve high or low, e.g., positive and negative, thresholds, or the absolute value of the sensed signal. In some examples, the device detects saturation if the signal meets the threshold for a threshold amount of time or number of consecutive samples, or if X of the last Y samples meet or exceed the threshold. The threshold may be a limit of the amplifier or another component of a sensing channel, or some predefined threshold less than the amplitude limit of the sensing channel. In some examples, the saturation threshold is a maximum or minimum allowed value of the signal, such as a maximum or minimum imposed by clamping circuitry of the device, e.g., IMD. In some examples, the device determines if the sensed signal is saturated by processing a digitized version of the signal.

In examples in which the integrity test comprises one or more lead impedance measurements, the device may compare the measurements to an impedance threshold to identify a possible lead-related condition. The threshold may be a predetermined value, or a value determined by the device based on other, previous impedance measurements, such as an average of previous impedance measurements. The previous measurements may have been periodically taken, or taken in response to events such as saturation of the sensed signal. In some examples, the device averages or otherwise combines the current measurement(s) with previous measurements, and compares the combined value, e.g., average, to an impedance threshold. If the device identifies a lead-related condition, the device may, as examples, provide an alert, change a sensing configuration, e.g., an electrode combination used for sensing, change a therapy configuration, or withhold a therapy.

In one example, the disclosure provides a method comprising sensing a physiological signal of a patient via one or more electrodes on at least one implantable medical lead, detecting saturation of the signal, and triggering a lead integrity test of the implantable medical lead in response to the detection.

In another example, the disclosure provides a system that includes an implantable medical lead comprising one or more electrodes, an implantable medical device (IMD) coupled to the lead that senses a physiological signal of a patient via the electrodes, and a processor. The processor detects saturation of the signal, and controls the IMD to perform a lead impedance measurement of the implantable medical lead in response to the detection.

In another example, the disclosure provides a computer-readable medium having instructions that cause a processor to detect saturation of a physiological signal of a patient sensed via one or more electrodes on at least one implantable medical lead, and trigger a lead integrity test of the implantable medical lead in response to the detection.

In another example, the disclosure provides a system that includes means for sensing a physiological signal of a patient via one or more electrodes on at least one implantable medical lead, means for detecting saturation of the signal, and means for triggering a lead integrity test of the implantable medical lead in response to the detection.

The details of one or more examples are set forth in the accompanying drawings and the description below. Other features, objects, and advantages of the disclosure will be apparent from the description and drawings, and from the claims.

DETAILED DESCRIPTION

Lead integrity tests are performed on implanted medical leads attached to an implanted medical device (IMD) to detect any lead-related condition that may affect sensing of a patient condition or therapy delivery. Typically, lead integrity testing involves measuring the impedance of one or more electrical paths, each path comprising two or more implanted electrodes on one or more implanted medical leads. Lead integrity testing may also involve comparing the measured impedance to a threshold in order to determine whether the lead(s) have a lead-related condition. This integrity testing may be performed periodically during therapy, e.g., while the patient is sleeping, in order to monitor the lead integrity as the patient moves and subjects the leads to mechanical stresses.

Periodic lead integrity testing is beneficial, but additional testing may provide additional benefits with respect to monitoring lead integrity. For example, a lead integrity test triggered by an event that may indicate a lead-related condition may be more likely to detect an intermittent lead-related condition. As described herein, lead integrity testing may be triggered upon detecting saturation of a signal sensed via the lead(s), such as a cardiac electrogram (EGM) signal. When the EGM signal reaches a threshold value, e.g., a substantially maximum or minimum amplitude, this value indicates that the EGM signal is saturated. Since the EGM amplitude range is generally defined to be larger than any physiological signal from the patient, EGM saturation may be indicative of a lead-related condition instead of a physiological event. Therefore, detecting EGM saturation may be an appropriate event to trigger performance of a lead integrity test.

In some examples, impedance measurements may be performed in response to cardiac EGM saturation detection. In one example, the impedance measurements may be performed at least partially during EGM saturation. In another example, the impedance measurements may be performed after the EGM saturation has ended. In any case, the impedance measurements are performed while the implanted medical leads are functioning to sense cardiac events. If the impedance measurements indicate a lead-related condition, the IMD may provide an alert, change a sensing configuration, change a therapy configuration, or withhold any responsive therapeutic shocks to the patient.

Figure 1:
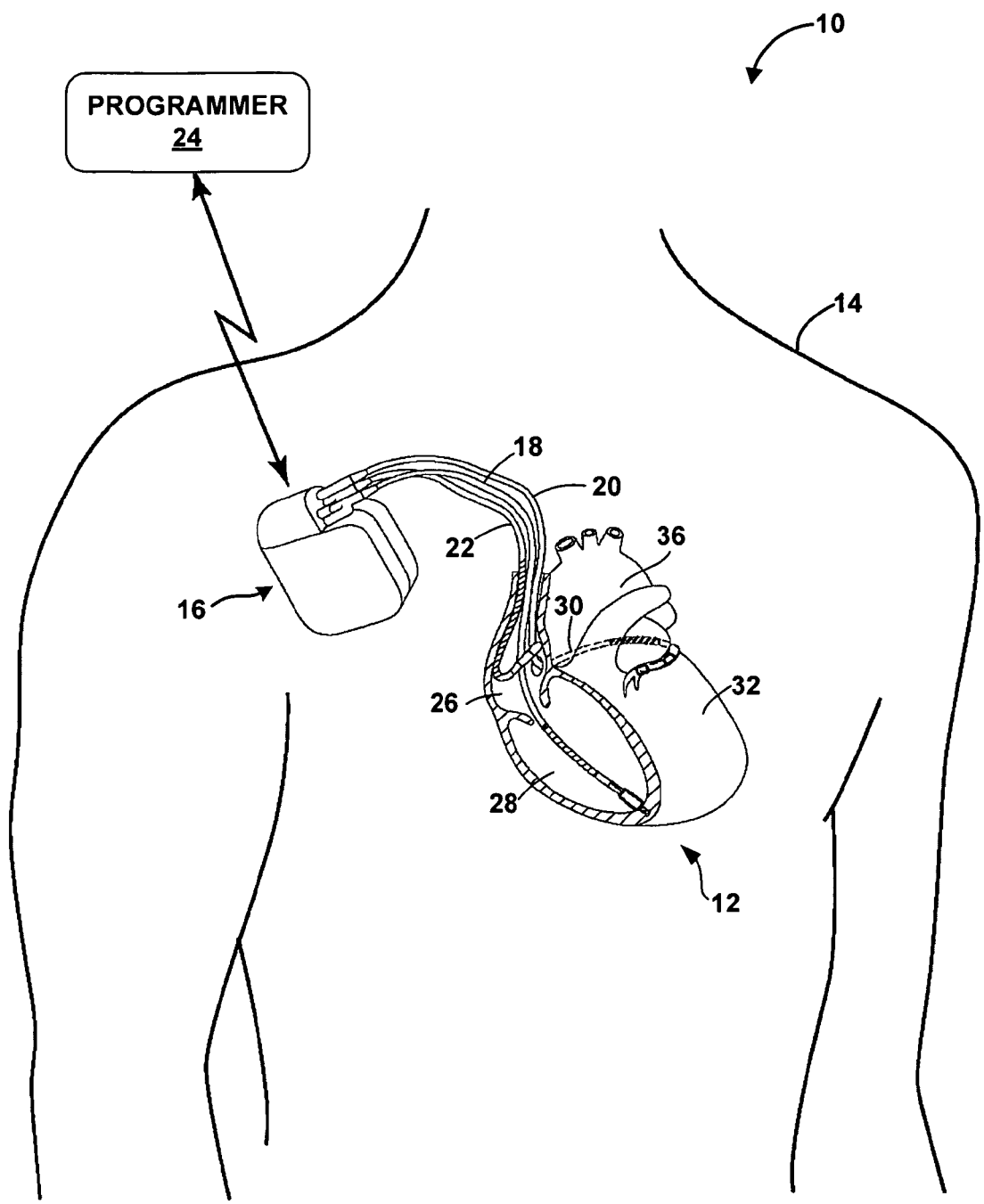
FIG. 1 is a conceptual drawing illustrating an example system that includes an implantable medical device (IMD) coupled to implantable medical leads.

FIG. 1 is a conceptual diagram illustrating an example system 10 that may be used for sensing of physiological parameters of patient 14 and/or to provide therapy to heart 12 of patient 14. Therapy system 10 includes IMD 16, which is coupled to leads 18, 20, and 22, and programmer 24. IMD 16 may be, for example, an implantable pacemaker, cardioverter, and/or defibrillator that provides electrical signals to heart 12 via electrodes coupled to one or more of leads 18, 20, and 22. Patient 14 is ordinarily, but not necessarily, a human patient.

Leads 18, 20, 22 extend into the heart 12 of patient 16 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12.

In some examples, therapy system 10 may additionally or alternatively include one or more leads or lead segments (not shown in FIG. 1) that deploy one or more electrodes within the vena cava or other vein. These electrodes may allow alternative electrical sensing configurations that may provide improved or supplemental sensing in some patients. Furthermore, in some examples, therapy system 10 may include temporary or permanent epicardial or subcutaneous leads, instead of or in addition to leads 18, 20 and 22. Such leads may be used for one or more of cardiac sensing, pacing, or cardioversion/defibrillation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar. IMD 16 may detect arrhythmia of heart 12, such as tachycardia or fibrillation of ventricles 28 and 32, and may also provide defibrillation therapy and/or cardioversion therapy via electrodes located on at least one of the leads 18, 20, 22. In some examples, IMD 16 may be programmed to deliver a progression of therapies, e.g., pulses with increasing energy levels, until a fibrillation of heart 12 is stopped. IMD 16 detects fibrillation employing one or more fibrillation detection techniques known in the art. As described herein, IMD 16 may also perform a lead integrity test in response to detecting EGM signal saturation during cardiac event sensing, in order to evaluate the integrity of leads 18, 20, and 22 that sensed the EGM signal saturation. The lead integrity test responsive to EGM signal saturation may be in addition to, or instead of, periodic lead integrity tests.

In some examples, programmer 24 may be a handheld computing device, computer workstation, or networked computing device. Programmer 24 may include a user interface that receives input from a user. The user interface may include, for example, a keypad and a display, which may for example, be a cathode ray tube (CRT) display, a liquid crystal display (LCD) or light emitting diode (LED) display. The keypad may take the form of an alphanumeric keypad or a reduced set of keys associated with particular functions. Programmer 24 can additionally or alternatively include a peripheral pointing device, such as a mouse, via which a user may interact with the user interface. In some embodiments, a display of programmer 24 may include a touch screen display, and a user may interact with programmer 24 via the display. It should be noted that the user may also interact with programmer 24 remotely via a networked computing device.

A user, such as a physician, technician, surgeon, electrophysiologist, or other clinician, may interact with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. As another example, the user may use programmer 24 to retrieve information from IMD 16 regarding other sensed physiological parameters of patient 14, such as intracardiac or intravascular pressure, activity, posture, respiration, or thoracic impedance. As another example, the user may use programmer 24 to retrieve information from IMD 16 regarding the performance or integrity of IMD 16 or other components of system 10, such as leads 18, 20 and 22, or a power source of IMD 16. In some examples, this information may be presented to the user as an alert. For example, a lead-related condition indicated by a lead integrity test by IMD 16 may cause programmer 24 to provide an alert to a user.

The user may use programmer 24 to program a therapy progression, select electrodes used to deliver defibrillation pulses, select waveforms for the defibrillation pulse, or select or configure a fibrillation detection algorithm for IMD 16. The user may also use programmer 24 to program aspects of other therapies provided by IMD 14, such as cardioversion or pacing therapies. In some examples, the user may activate certain features of IMD 16 by entering a single command via programmer 24, such as depression of a single key or combination of keys of a keypad or a single point-and-select action with a pointing device.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
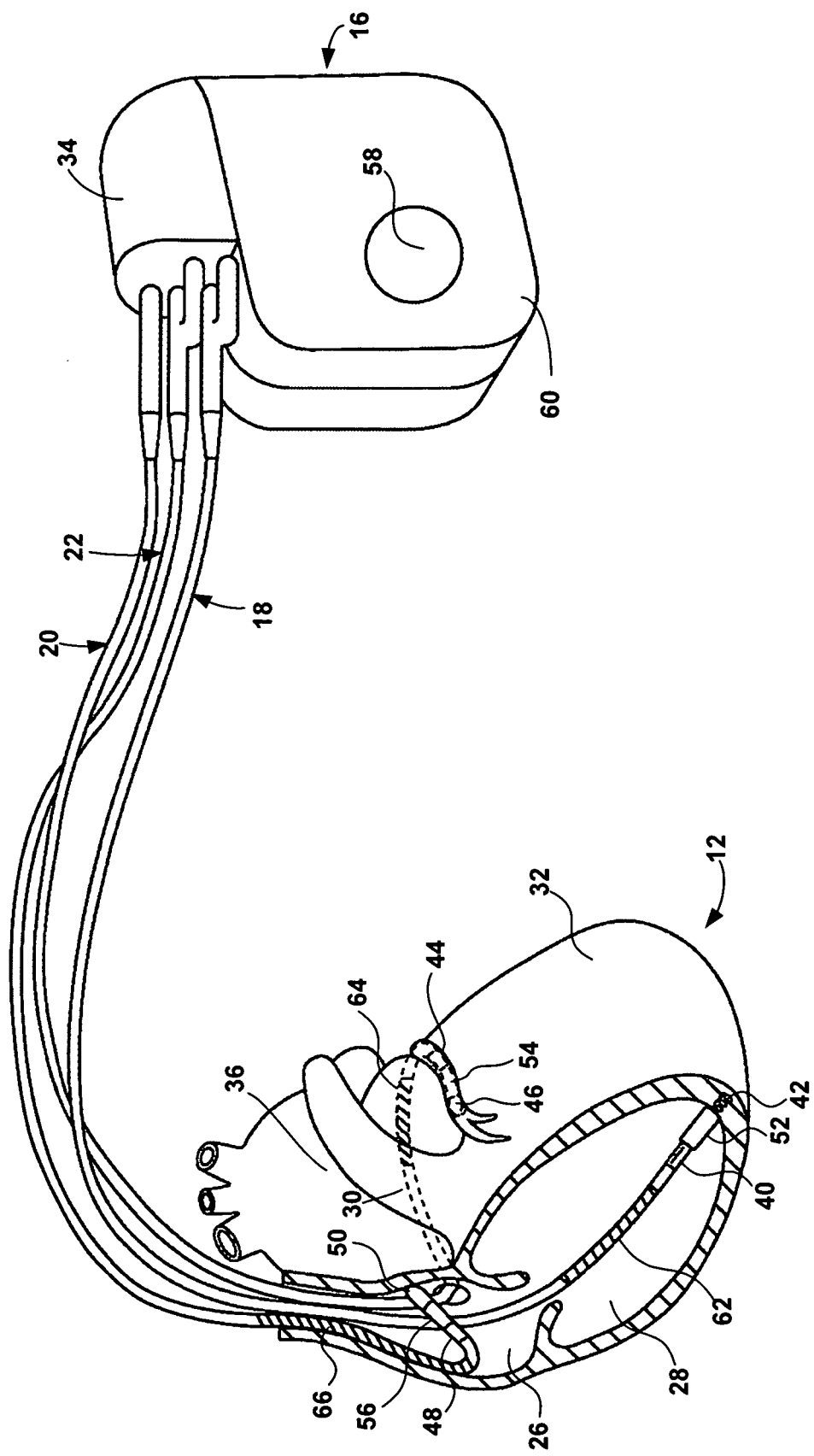
FIG. 2 is a conceptual drawing illustrating the example IMD and leads of FIG. 1 in conjunction with a heart.

FIG. 2 is a conceptual diagram illustrating IMD 16 and leads 18, 20 and 22 of therapy system 10 in greater detail. Leads 18, 20, 22 may be electrically coupled to a signal generator, e.g., stimulation generator, and a sensing module of IMD 16 via connector block 34. In some examples, proximal ends of leads 18, 20, 22 may include electrical contacts that electrically couple to respective electrical contacts within connector block 34 of IMD 16. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in coronary sinus 30 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44 and 48 may take the form of ring electrodes, and electrodes 42, 46 and 50 may take the form of extendable helix tip electrodes mounted retractably within insulative electrode heads 52, 54 and 56, respectively. In other embodiments, one or more of electrodes 42, 46 and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64 and 66 may be electrically coupled to a respective one of the coiled conductors within the lead body of its associated lead 18, 20, 22, and thereby coupled to respective ones of the electrical contacts on the proximal end of leads 18, 20 and 22.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 62, 64 and 66. The electrical signals are conducted to IMD 16 from the electrodes via the respective leads 18, 20, 22. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 58. The sensed electrical signals may be processed as the EMG signal by IMD 16.

Any combination of electrodes 40, 42, 44, 46, 48, 50, 58, 62, 64 and 66 may be considered a sensing configuration that has one or more electrodes. In some examples, a sensing configuration may be a bipolar electrode combination on the same lead, such as electrodes 40 and 42 of lead 18. On one lead having three electrodes, there may be three different sensing configurations available to IMD 16. These sensing configurations are, for the example of lead 18, tip electrode 42 and ring electrode 40, tip electrode 42 and elongated electrode 62, and ring electrode 40 and elongated electrode 62. These sensing configurations may be considered near-field configurations. However, some embodiments may utilize sensing configurations having electrodes of two different leads. Furthermore, a sensing configuration may utilize housing electrode 58 as one of the electrodes. These sensing configurations utilizing at least one electrode away from heart 12, e.g., elongated electrode 62 and housing electrode 58 or housing electrode 58 and another housing electrode (not shown), may be considered far-field configurations. In any sensing configuration, the polarity of each electrode in the sensing configuration may be configured as appropriate for the application of the sensing configuration.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration. Furthermore, IMD 16 may deliver cardioversion or defibrillation pulses to heart 12 via any combination of elongated electrodes 62, 64, 66, and housing electrode 58. Electrodes 58, 62, 64, 66 may also be used to deliver cardioversion pulses, e.g., a responsive therapeutic shock, to heart 12. Electrodes 62, 64, 66 may be fabricated from any suitable electrically conductive material, such as, but not limited to, platinum, platinum alloy or other materials known to be usable in implantable defibrillation electrodes.

The configuration of therapy system 10 illustrated in FIGS. 1 and 2 is merely one example. In other examples, a therapy system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
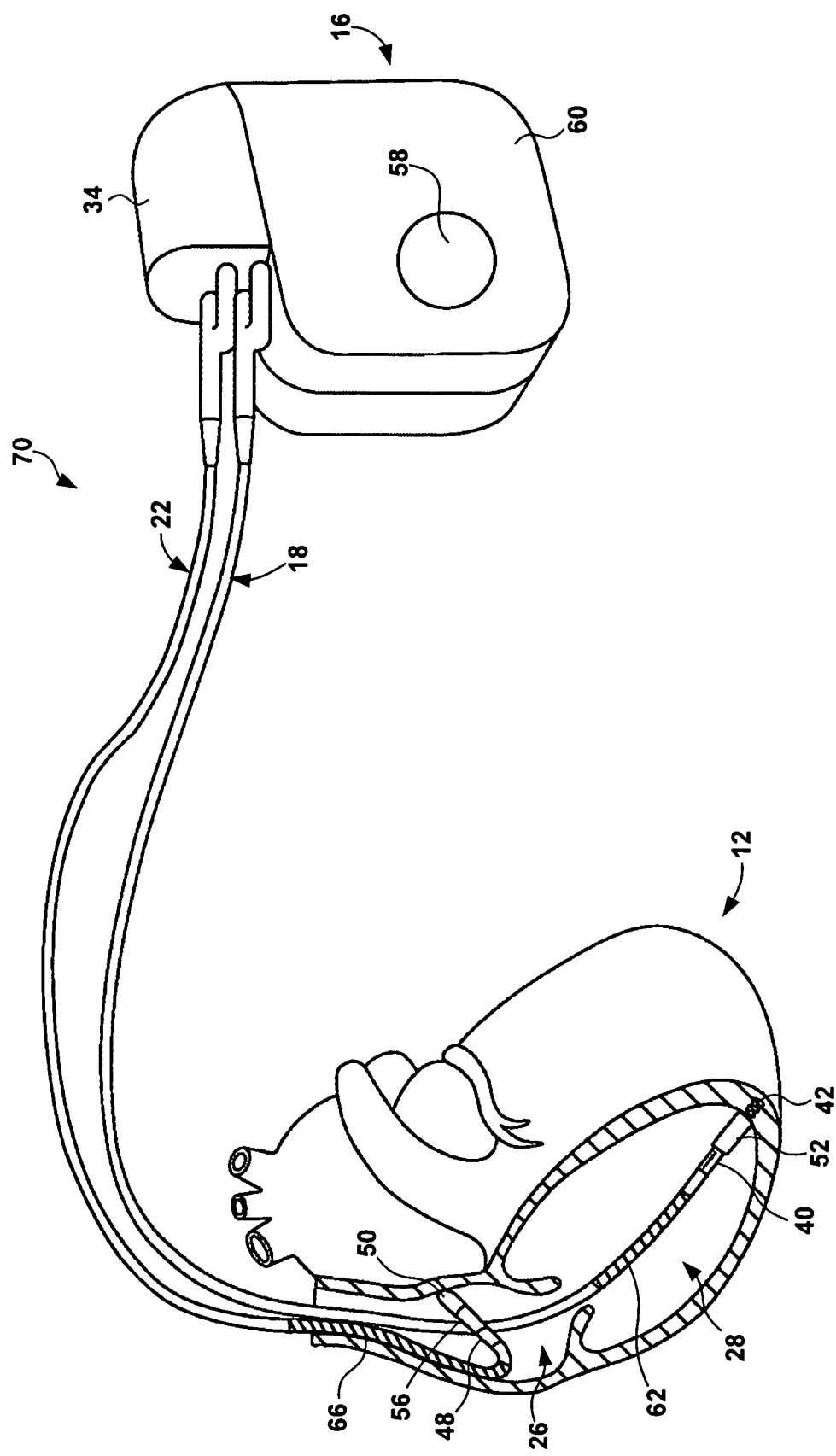
FIG. 3 is a conceptual drawing illustrating the example IMD of FIG. 1 coupled to a different example configuration of two implantable medical leads in conjunction with a heart.

In addition, in other examples, a therapy system may include any suitable number of leads coupled to IMD 16, and each of the leads may extend to any location within or proximate to heart 12. For example, other examples of therapy systems may include three transvenous leads located as illustrated in FIGS. 1 and 2, and an additional lead located within or proximate to left atrium 36. As another example, other examples of therapy systems may include a single lead that extends from IMD 16 into right atrium 26 or right ventricle 28, or two leads that extend into a respective one of the right ventricle 26 and right atrium 26. An example of this type of therapy system is shown in FIG. 3. Any electrodes located on these additional leads may be used in sensing configurations that may be subject to a lead integrity test responsive to EMG signal saturation.

FIG. 3 is a conceptual diagram illustrating another example of therapy system 70, which is similar to therapy system 10 of FIGS. 1 and 2, but includes two leads 18, 22, rather than three leads. Leads 18, 22 are implanted within right ventricle 28 and right atrium 26, respectively. Therapy system 70 shown in FIG. 3 may be useful for providing defibrillation and pacing pulses to heart 12. Lead integrity testing according to this disclosure may be performed in two lead systems in the manner described herein with respect to three lead systems.

Figure 4:
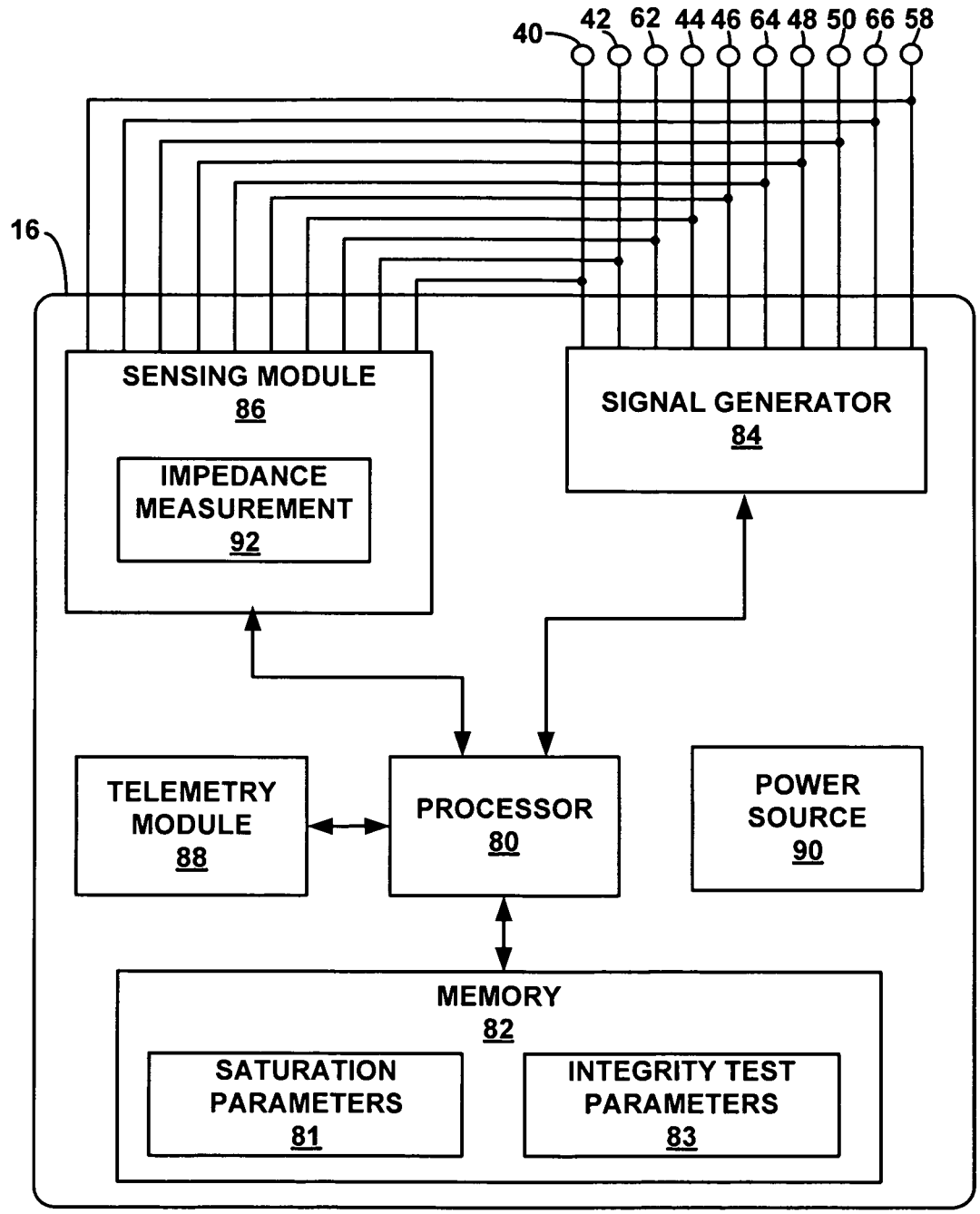
FIG. 4 is a functional block diagram illustrating an example configuration of the IMD of FIG. 1.

FIG. 4 is a functional block diagram illustrating an example configuration of IMD 16. In the illustrated example, IMD 16 includes a processor 80, memory 82, signal generator 84, sensing module 86, telemetry module 88, and power source 90. Memory 82 includes computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or analog logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof.

Processor 80 controls signal generator 84 to deliver stimulation therapy to heart 12 according to a selected one or more of therapy programs, which may be stored in memory 82. For example, processor 80 may control signal generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. Signal generator 84 is configured to generate and deliver electrical stimulation therapy to heart 12. For example, signal generator 84 may deliver defibrillation shocks as therapy to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. In some examples, signal generator 84 delivers pacing, cardioversion, or defibrillation stimulation in the form of electrical pulses. In other examples, signal generator may deliver one or more of these types of stimulation in the form of other signals, such as sine waves, square waves, or other substantially continuous time signals.

Signal generator 84 may include a switch module, and processor 80 may use the switch module to select, e.g., via a data/address bus, which of the available electrodes are used to deliver defibrillation pulses or pacing pulses. The switch module may include a switch array, switch matrix, multiplexer, or any other type of switching device suitable to selectively couple stimulation energy to selected electrodes.

Electrical sensing module 86 monitors signals from at least one of electrodes 40, 42, 44, 46, 48, 50, 58, 62, 64 or 66 in order to monitor electrical activity of heart 12. Sensing module 86 may also include a switch module to select which of the available electrodes are used to sense the heart activity, depending upon which electrode combination is used in the current sensing configuration. In some examples, processor 80 may select the electrodes that function as sense electrodes, i.e., select the sensing configuration, via the switch module within sensing module 86. Processor 80 may control the functionality of sensing module 86 by providing signals via a data/address bus.

Sensing module 86 may include one or more detection channels, each of which may comprise an amplifier. The detection channels may be used to sense the cardiac signals. Some detection channels may detect cardiac events, such as R- or P-waves, and provide indications of the occurrences of such events to processor 80. One or more other detection channels may provide the signals to an analog-to-digital converter, for processing or analysis by processor 80. In response to the signals from processor 80, the switch module within sensing module 86 may couple selected electrodes to selected detection channels.

For example, sensing module 86 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 80 then uses that detection in measuring frequencies of the sensed events. Different narrow band channels of sensing module 86 may have distinct functions. For example, some various narrow band channels may be used to sense either atrial or ventricular events. In other examples, one or more of the narrow band channels may include more than one narrow band filtered sense-amplifier, such that the narrow band channel can additionally detect whether the sensed signal has met or exceeded saturation threshold for the EMG signal, and provide a saturation indication to processor 80.

In one example, at least one narrow band channel may include an R-wave amplifier that receives signals from the sensing configuration of electrodes 40 and 42, which are used for sensing and/or pacing in right ventricle 28 of heart 12. Another narrow band channel may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

In some examples, sensing module 86 includes a wide band channel which may comprise an amplifier with a relatively wider pass band than the R-wave or P-wave amplifiers. Signals from the selected sensing electrodes that are selected for coupling to this wide-band amplifier may be converted to multi-bit digital signals by an analog-to-digital converter (ADC) provided by, for example, sensing module 86 or processor 80. In some examples, processor 80 may store signals the digitized versions of signals from the wide band channel in memory 82 as EGM signals. In some examples, the storage of such EGMs in memory 82 may be under the control of a direct memory access circuit. In addition, detection of EGM signal saturation may trigger the storage of a portion of the EGM signal that includes the saturation. Processor 80 may control memory 82 to store a portion of the EGM signal that includes the saturation event, e.g., a 1 second portion, a 10 second portion, or a 100 second portion.

In some examples, processor 80 may employ digital signal analysis techniques to characterize the digitized signals from the wide band channel to, for example detect and classify the patient's heart rhythm. Processor 80 may detect and classify the patient's heart rhythm by employing any of the numerous signal processing methodologies known in the art. Processor 80 may also processor the digitized signal to detect saturation of the EMG signal, which may be used for triggering a lead integrity test, including associated lead impedance measurements with an impedance measurement module 92.

If IMD 16 is configured to generate and deliver pacing pulses to heart 12, processor 80 may include pacer timing and control module, which may be embodied as hardware, firmware, software, or any combination thereof. The pacer timing and control module may comprise a dedicated hardware circuit, such as an ASIC, separate from other processor 80 components, such as a microprocessor, or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber that is sensed, and the third letter may indicate the chamber in which the response to sensing is provided.

Intervals defined by the pacer timing and control module within processor 80 may include atrial and ventricular pacing escape intervals, refractory periods during which sensed P-waves and R-waves are ineffective to restart timing of the escape intervals, and the pulse widths of the pacing pulses. As another example, the pace timing and control module may define a blanking period, and provide signals sensing module 86 to blank one or more channels, e.g., amplifiers, for a period during and after delivery of electrical stimulation to heart 12. The durations of these intervals may be determined by processor 80 in response to stored data in memory 82. The pacer timing and control module of processor 80 may also determine the amplitude of the cardiac pacing pulses.

During pacing, escape interval counters within the pacer timing/control module of processor 80 may be reset upon sensing of R-waves and P-waves with detection channels of sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one of the chambers of heart 12. Processor 80 may reset the escape interval counters upon the generation of pacing pulses by signal generator 84, and thereby control the basic timing of cardiac pacing functions, including anti-tachyarrhythmia pacing.

The value of the count present in the escape interval counters when reset by sensed R-waves and P-waves may be used by processor 80 to measure the durations of R-R intervals, P-P intervals, PR intervals and R-P intervals, which are measurements that may be stored in memory 82. Processor 80 may use the count in the interval counters to detect a suspected tachyarrhythmia event, such as ventricular fibrillation or ventricular tachycardia.

In some examples, processor 80 may operate as an interrupt driven device, and is responsive to interrupts from pacer timing and control module, where the interrupts may correspond to the occurrences of sensed P-waves and R-waves and the generation of cardiac pacing pulses. Any necessary mathematical calculations to be performed by processor 80 and any updating of the values or intervals controlled by the pacer timing and control module of processor 80 may take place following such interrupts. A portion of memory 82 may be configured as a plurality of recirculating buffers, capable of holding series of measured intervals, which may be analyzed by processor 80 in response to the occurrence of a pace or sense interrupt to determine whether the patient's heart 12 is presently exhibiting atrial or ventricular tachyarrhythmia.

In some examples, an arrhythmia detection method may include any suitable tachyarrhythmia detection algorithms. In one example, processor 80 may utilize all or a subset of the rule-based detection methods described in U.S. Pat. No. 5,545,186 to Olson et al., entitled, "PRIORITIZED RULE BASED METHOD AND APPARATUS FOR DIAGNOSIS AND TREATMENT OF ARRHYTHMIAS," which issued on Aug. 13, 1996, or in U.S. Pat. No. 5,755,736 to Gillberg et al., entitled, "PRIORITIZED RULE BASED METHOD AND APPARATUS FOR DIAGNOSIS AND TREATMENT OF ARRHYTHMIAS," which issued on May 26, 1998. U.S. Pat. No. 5,545,186 to Olson et al. U.S. Pat. No. 5,755,736 to Gillberg et al. is incorporated herein by reference in their entireties. However, other arrhythmia detection methodologies may also be employed by processor 80 in other examples.

In some examples, processor 80 may determine that tachyarrhythmia has occurred by identification of shortened R-R (or P-P) interval lengths. Generally, processor 80 detects tachycardia when the interval length falls below 220 milliseconds (ms) and fibrillation when the interval length falls below 180 ms. These interval lengths are merely examples, and a user may define the interval lengths as desired, which may then be stored within memory 82. This interval length may need to be detected for a certain number of consecutive cycles, for a certain percentage of cycles within a running window, or a running average for a certain number of cardiac cycles, as examples.

In the event that processor 80 detects an atrial or ventricular tachyarrhythmia based on signals from sensing module 86, and an anti-tachyarrhythmia pacing regimen is desired, timing intervals for controlling the generation of anti-tachyarrhythmia pacing therapies by signal generator 84 may be loaded by processor 80 into the pacer timing and control module to control the operation of the escape interval counters therein and to define refractory periods during which detection of R-waves and P-waves is ineffective to restart the escape interval counters.

If IMD 16 is configured to generate and deliver cardioversion or defibrillation pulses to heart 12, signal generator 84 may include a high voltage charge circuit and a high voltage output circuit. In the event that generation of a cardioversion or defibrillation pulse is required, processor 80 may employ the escape interval counter to control timing of such cardioversion and defibrillation pulses, as well as associated refractory periods. In response to the detection of atrial or ventricular fibrillation or tachycardia requiring a cardioversion or defibrillation pulse, processor 80 may activate a cardioversion/defibrillation control module, which may, like pacer timing and control module, be a hardware component of processor 80 and/or a firmware or software module executed by one or more hardware components of processor 80. The cardioversion/defibrillation control module may initiate charging of the high voltage capacitors of the high voltage charge circuit of stimulation generator 84 under control of a high voltage charging control line.

Processor 80 may monitor the voltage on the high voltage capacitor may be monitored, e.g., via a voltage charging and potential (VCAP) line. In response to the voltage on the high voltage capacitor reaching a predetermined value set by processor 80, processor 80 may generate a logic signal that terminates charging. Thereafter, timing of the delivery of the defibrillation or cardioversion pulse by signal generator 84 is controlled by the cardioversion/defibrillation control module of processor 80. Following delivery of the fibrillation or tachycardia therapy, processor 80 may return signal generator 84 to a cardiac pacing function and await the next successive interrupt due to pacing or the occurrence of a sensed atrial or ventricular depolarization.

Signal generator 84 may deliver cardioversion or defibrillation pulses with the aid of an output circuit that determines whether a monophasic or biphasic pulse is delivered, whether housing electrode 58 serves as cathode or anode, and which electrodes are involved in delivery of the cardioversion or defibrillation pulses. Such functionality may be provided by one or more switches or a switching module of signal generator 84.

Intermittent fracture of one or more of leads 18, 20, 22 or disconnection of the lead pin from IMD 16 may be interpreted by IMD 16 as a plurality of sensed cardiac events, e.g., R-waves, and result in detection of a suspected tachyarrhythmia by IMD 16. More particularly, "make/break" events resulting from intermittent fracture or disconnection of a conductor within one of leads 18, 20, and 22 that is electrically connected to an electrode used in an electrode combination for a current sensing configuration may introduce noise into the signal received by a sensing channel of sensing module 86 that is electrically coupled to the electrode combination. These non-cardiac events may result in large amplitude EGM signals, such as saturation of the EGM signal. Although saturation of the EGM signal could actually be a cardiac event that requires IMD 16 intervention, lead impedance measurements triggered by the saturation may quickly determine if leads of the sensing configuration are functioning correctly.

In some examples, processor 80 may control measurement of one or more impedances of one or more leads 18, 20, and 22. In some examples, processor 80 may control impedance measurement module 92 to measure lead impedances during the detected saturation of the EGM signal. In this manner, processor 80 may be capable of identifying the lead integrity when the saturated EGM signal is produced. In some examples, processor 80 may control impedance measurement module 92 to measure lead impedances after the saturation of the EGM signal has ended. Since impedance measurements may not be possible during EGM saturation, or the saturation of the EGM signal is too short to conduct impedance measurements, the lead integrity test may still provide up-to-date lead integrity information, and may detect an intermittent lead-related condition.

In some examples, sensing module 86 and/or processor 80 are capable of collecting, measuring, and/or calculating impedance data for any of a variety of electrical paths that include two or more of electrodes 40, 42, 44, 46, 48, 50, 58, 62, 64 and 66. In the illustrated example, sensing module 86 comprises an impedance measurement module 92, which may measure electrical parameter values during delivery of an electrical signal between at least two of the electrodes. Processor 80 may control signal generator 84 to deliver the electrical signal between the electrodes. Processor 80 may determine impedance values based on parameter values measured by impedance measurement module 92, and store measured impedance values in memory 82.

In some examples, processor 80 may perform an impedance measurement by controlling delivery, from signal generator 84, of a voltage pulse between first and second electrodes. Measurement module 92 may measure a resulting current, and processor 80 may calculate a resistance based upon the voltage amplitude of the pulse and the measured amplitude of the resulting current. In other examples, processor 80 may perform an impedance measurement by controlling delivery, from signal generator 84, of a current pulse between first and second electrodes. Measurement module 92 may measure a resulting voltage, and processor 80 may calculate a resistance based upon the current amplitude of the pulse and the measured amplitude of the resulting voltage. Measurement module 92 may include circuitry for measuring amplitudes of resulting currents or voltages, such as sample and hold circuitry.

In these examples, signal generator 84 delivers signals that do not necessarily deliver stimulation therapy to heart 12, due to, for example, the amplitudes of such signals and/or the timing of delivery of such signals. For example, these signals may comprise sub-threshold amplitude signals that may not stimulate heart 12. In some cases, these signals may be delivered during a refractory period, in which case they also may not stimulate heart 12. IMD 16 may use defined or predetermined pulse amplitudes, widths, frequencies, or electrode polarities for the pulses delivered for these various impedance measurements. In some examples, the amplitudes and/or widths of the pulses may be sub-threshold, e.g., below a threshold necessary to capture or otherwise activate tissue, such as cardiac tissue of heart 16.

In certain cases, IMD 16 may collect impedance values that include both a resistive and a reactive (i.e., phase) component. In such cases, IMD 16 may measure impedance during delivery of a sinusoidal or other time varying signal by signal generator 84, for example. Thus, as used herein, the term "impedance" is used in a broad sense to indicate any collected, measured, and/or calculated value that may include one or both of resistive and reactive components.

In response to detection of EGM saturation, processor 80 may control a plurality of measurements of the impedance of the sensing configuration involved with generating the EGM signal that is saturated, e.g., the impedance of an electrical path that includes the electrode combination coupled to the detection channel of sensing module 86 that generated the EGM signal. Impedance measurements for the sensing configuration may indicate whether an integrity issue for the sensing configuration exists, which may have resulted in the saturation of the EGM signal from the sensing configuration. However, in other examples, processor 80 may control a plurality of measurements of the impedance of any one or more electrical paths including combinations of electrodes 40, 42, 44, 46, 48, 50, 58, 62, 64 and 66 in response to detection of the EGM signal saturation.

Processor 80 may detect EGM signal saturation according to saturation parameters 81 stored within memory 82. Saturation parameters 81 may include one or more saturation thresholds, to which processor 80 may compare a digitized version of an EGM to detect saturation. In some examples, saturation thresholds may define saturation as any EGM signal equaling the maximum or minimum amplitude limit of sensing module 86, e.g., imposed by a clamping circuit. In addition, saturation parameters 81 may include a saturation duration that defines the number of samples or length of time that the EGM meets the saturation threshold, or the percentage of samples within a running window, or an X of the last Y samples at the threshold, before processor 80 detects the saturation of the EGM signal. Saturation parameters 81 may also indicate which channel of sensing module 86 may be used to detect saturation of the EGM signal, or any other sensing parameters necessary for accurately detecting saturation of the EGM signal.

Processor 80 may control signal generator 84 to deliver the test pulses for impedance measurement according to integrity test parameters 83 stored in memory 82. For example, processor 80 may control the timing or amplitude of test pulses based on integrity test parameters 83. Integrity test parameters 83 may, in some examples, specify a period of time, e.g., a window, subsequent a detected event, which may be an R-wave, noise, or EGM signal saturation, in which one or more test pulses may be delivered. The duration of the period may be selected to be less than a typical tachyarrhythmia cycle length for patient 16 or patients in general, less than a typical EGM signal saturation duration, short as possible to detect impedance, or as appropriate to determine the most accurate impedance values. Furthermore, by controlling the timing of test pulses in this manner, interference with the accuracy of impedance measurements by intrinsic cardiac signals may be avoided. Processor 80 may compare the impedances measured from each of the test pulses to an impedance threshold, and evaluates the integrity of the sensing configuration, or more generally lead integrity, based upon the comparison.

Processor 80 may, for example, withhold delivery of any therapeutic stimulation or responsive therapeutic shock in response to determining that a sensed cardiac event from the EGM signal may have been due to saturation of the EGM signal and that such saturation was due to a lead-related condition affecting the sensing configuration. Withholding delivery of any stimulation or shock may continue until lead integrity is ruled out or may essentially be a cancellation of any stimulation or shock to be delivered. If the integrity test indicates that there is no problem with the sensing configuration, stimulation may be allowed to be delivered immediately or only upon identifying the reason for the EGM signal saturation. For example, the allowable amplitude range for the detection channel that received the EGM signal may need to be increased to address unusually large physiological signals, for example.

Processor 80 may allow a responsive therapeutic shock to be delivered to patient 14 if the lead integrity test indicates that there are lead-related conditions, or no lead-related conditions with the sensing configuration that detected a tachyarrhythmia or the electrode combination used for delivery of responsive therapy. However, processor 80 may also run additional tests on other components of IMD 16. For example, processor 80 may perform tests on signal generator 84, sensing module 86, or any other component that may be responsible for EGM signal saturation. An amplifier of sensing module 86 or impedance measurement module 92 may need recalibration, or processor 80 may determine that an outside electrical field produced the EGM signal saturation. In these cases, processor 80 may continue to provide therapy to patient 14.

In other examples, processor 80 may also switch from the current sensing configuration to an alternative sensing configuration in response to determining that the detection of the EGM signal saturation may have been due to an integrity issue with the sensing configuration. Processor 80 may select the alternative sensing configuration from a list of available sensing configurations stored in memory 82. In some examples, multiple sensing configurations, e.g., electrode combinations, may be tested in response to the detection of the EGM signal saturation, and a sensing configuration that does not exhibit an integrity issue may be selected.

Additionally, processor 80 may change the shock configuration if the integrity test indicates a potential issue with the shock configuration delivering effective therapy to patient 14. For example, if the sensing configuration utilizes one or more electrodes also used to deliver a shock, processor 80 may switch to an alternative shock configuration that no longer includes the one or more electrodes.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and the control signals for the telemetry circuit within telemetry module 88, e.g., via an address/data bus. In some examples, telemetry module 88 may provide received data to processor 80 via a multiplexer.

In some examples, processor 80 may transmit atrial and ventricular heart signals (e.g., electrocardiogram signals) produced by atrial and ventricular sense amp circuits within sensing module 86 to programmer 24. Programmer 24 may interrogate IMD 16 to receive the heart signals. Processor 80 may store heart signals within memory 82, and retrieve stored heart signals from memory 82. Processor 80 may also generate and store marker codes indicative of different cardiac events that sensing module 86 detects, and transmit the marker codes to programmer 24. An example pacemaker with marker-channel capability is described in U.S. Pat. No. 4,374,382 to Markowitz, entitled, "MARKER CHANNEL TELEMETRY SYSTEM FOR A MEDICAL DEVICE," which issued on Feb. 15, 1983 and is incorporated herein by reference in its entirety.

In addition, processor 80 may transmit integrity testing information to programmer 24 via telemetry module 88. In some examples, telemetry module 88 may transmit an alert to programmer 24 indicating an integrity issue with the sensing configuration, or programmer 24 may provide such an alert in response to the testing information received from IMD 16. This alert may prompt the user to reprogram IMD 16 to use a different sensing or therapy configuration, or perform some other function to address the possible integrity issue. In some examples, IMD 16 may signal programmer 24 to further communicate with and pass the alert through a network such as the Medtronic CareLink® Network developed by Medtronic, Inc., of Minneapolis, Minn., or some other network linking patient 14 to a clinician. In some examples, telemetry module 88 may transmit an alert to programmer 24 when saturation of the EGM signal has been detected. The alert may be immediately presented to the user of programmer 24 or logged in a saturation log that indicates each time that saturation of the EGM signal was detected. The alert may be accompanied by an EGM and marker channel illustrating the saturation, which may have been stored in memory 82, as described above.

The various components of IMD 16 are coupled to power source 90, which may include a rechargeable or non-rechargeable battery. A non-rechargeable battery may be capable of holding a charge for several years, while a rechargeable battery may be inductively charged from an external device, e.g., on a daily or weekly basis.

Figure 5:
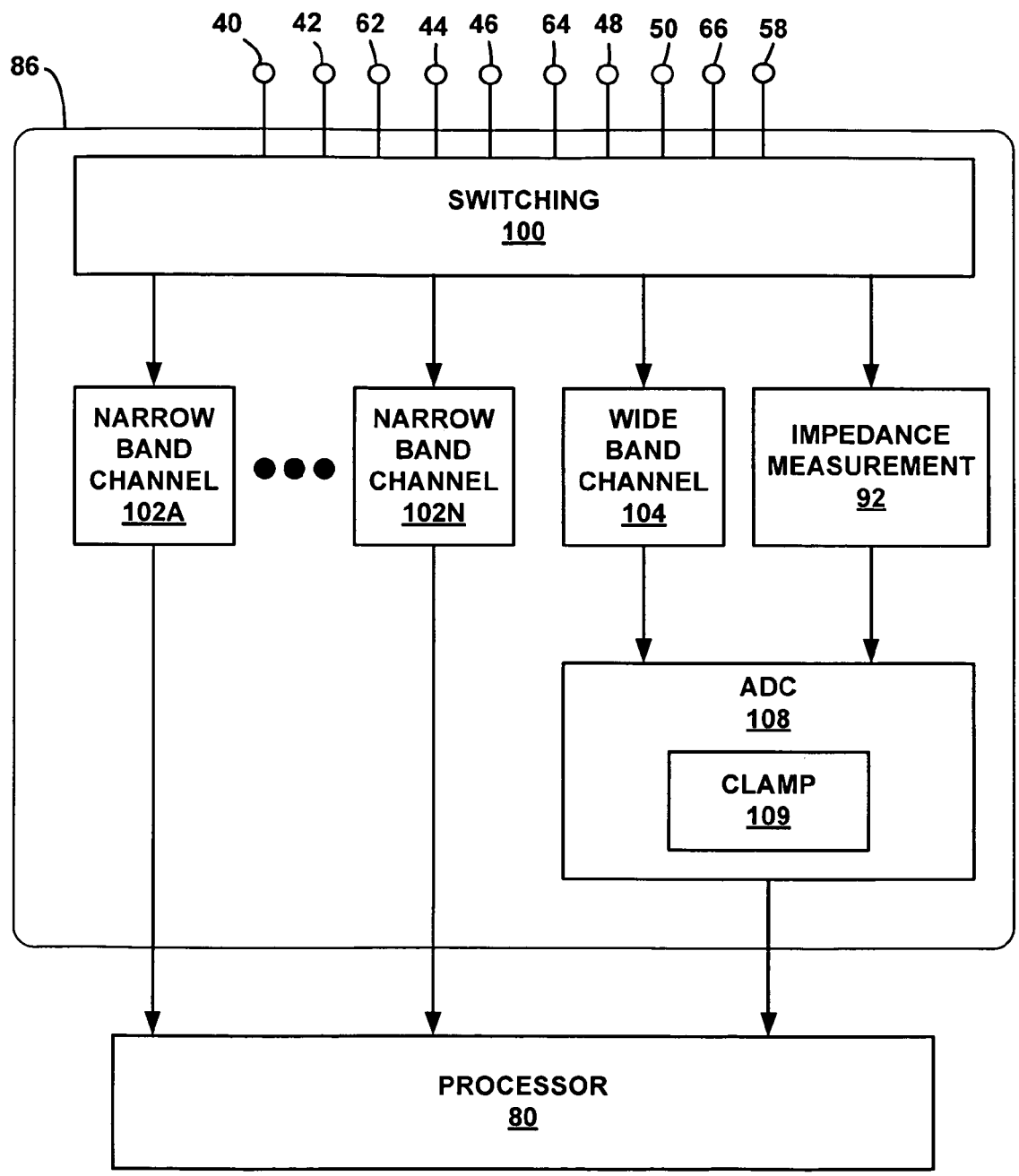
FIG. 5 is a functional block diagram illustrating an example electrical sensing module having multiple detection channels.

FIG. 5 is a block diagram of an example configuration of electrical sensing module 86. As shown in FIG. 5, electrical sensing module 86 includes multiple components including switching module 100, narrow band channels 102A to 102N, wide band channel 104, impedance measurement module 92, and analog to digital converter (ADC) 108. Switching module 100 may, based on control signals from processor 80, control which of electrodes 40, 42, 44, 46, 48, 50, 58, 62, 64 and 66 is coupled to which of channels 102 and 104 and impedance measurement module 92, at any given time. Switching module 100 may comprise a multiplexer, and in some examples may comprise a transistor array, an array of microelectromechanical switches, or the like.

Each of narrow band channels 102 may comprise a narrow band filtered sense-amplifier that compares the detected signal to a threshold. If the filtered and amplified signal is greater than the threshold, the narrow band channel indicates that a certain electrical heart event has occurred.

Processor 80 then uses that detection in measuring frequencies of the detected events. Narrow band channels 102 may have distinct functions. For example, some various narrow band channels may be used to detect either atrial or ventricular events.

In one example, at least one narrow band channel 102 may include an R-wave amplifier that receives signals from the sensing configuration of electrodes 40 and 42, which are used for sensing and/or pacing in right ventricle 28 of heart 12. Another narrow band channel 102 may include another R-wave amplifier that receives signals from the sensing configuration of electrodes 44 and 46, which are used for sensing and/or pacing proximate to left ventricle 32 of heart 12. In some examples, the R-wave amplifiers may take the form of an automatic gain controlled amplifier that provides an adjustable sensing threshold as a function of the measured R-wave amplitude of the heart rhythm.

In addition, in some examples, a narrow band channel 102 may include a P-wave amplifier that receives signals from electrodes 48 and 50, which are used for pacing and sensing in right atrium 26 of heart 12. In some examples, the P-wave amplifier may take the form of an automatic gain controlled amplifier that provides an adjustable sensing threshold as a function of the measured P-wave amplitude of the heart rhythm. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Other amplifiers may also be used. Furthermore, in some examples, one or more of the sensing channels of sensing module 86 may be selectively coupled to housing electrode 58, or elongated electrodes 62, 64, or 66, with or instead of one or more of electrodes 40, 42, 44, 46, 48 or 50, e.g., for unipolar sensing of R-waves or P-waves in any of chambers 26, 28, or 32 of heart 12.

Narrow band channels 102 may additionally include one or more channels, separate from a P-wave amplifier or an R-wave amplifier. These additional channels 102 may be coupled to a sensing configuration (electrode combination) for P- or R-wave detection in parallel with a narrow band channel 102 for P- or R-wave detection. These additional channels may include amplifiers configured with a sensing threshold for detecting when the EGM signal is saturated. These additional narrow band channels may output signals indicating EGM saturation to processor 80. If processor 80 detects EGM signal saturation from narrow band channel 102, processor 80 may trigger a lead integrity test in response to the EGM signal saturation.

As described above, wide band channel 104 may comprise an amplifier with a relatively wider pass band than the R-wave or P-wave amplifiers. Signals from the selected sensing electrodes that are selected for coupling to this wide-band amplifier may be converted to multi-bit digital signals by ADC 108. In some examples, processor 80 may analyze the digital signal detect EGM saturation. For example, processor 80 may couple wide band channel 104 to a sensing configuration (electrode combination) in parallel with one of a narrow band channels 102 for P- or R-wave detection in order to analyze the EGM signal from the sensing configuration for saturation. Processor 80 may compare the digitized EGM signal to one or more thresholds to detect saturation, as described above.

As illustrated in FIG. 5, ADC 108 may comprise or be coupled to a clamp circuit 109. In other examples, wide band channel 104 may comprise clamp circuit 109. Clamp circuit 109 may constrain the EGM signal provided to components within ADC to be between a maximum amplitude value and a minimum amplitude value. When the EGM meets or exceeds the maximum or minimum amplitude, it may be considered saturated. In some examples, amplitude thresholds used by processor 80 to detect saturation are substantially equal to the maximum or minimum defined by clamp circuit 109. In other examples, processor 80 may receive an indication of whether the signal is clamped from clamp circuit 109, and may detect saturation of the EGM based on the clamped indication from the clamp circuit.

In response to determining that the EGM signal is saturated, processor 80 may control impedance measurement module 92 to measure the impedance (or other electrical parameters) of one or more electrical paths defined by one or electrode combinations (sensing configurations), as described above. Processor 80 may control switching module 100 to sequentially couple impedance measurement module 92 to the different electrode combinations for the desired measurements. Processor 80 may, for example, receive digitized versions of voltage or current values measured by impedance measurement module 92 from ADC 108, and determine impedances for the electrode combinations based on the digitized values.

In one embodiment, processor 80 may analyze the measured impedance values, e.g., compare these values, or other values determined based on the values, such as mean or median values, to one or more thresholds and identify any possible conditions with one or more sensing configurations. For example, IMD 16 may, as a result of one or more comparisons, determine that one or more of leads 18, 20, and 22 has a lead-related condition, or more specifically that one or more electrodes or associated conductors within the leads may have an integrity issue. Processor 80 may send impedance measurement and/or analysis data to programmer 24 via telemetry module 88.

Figure 6:
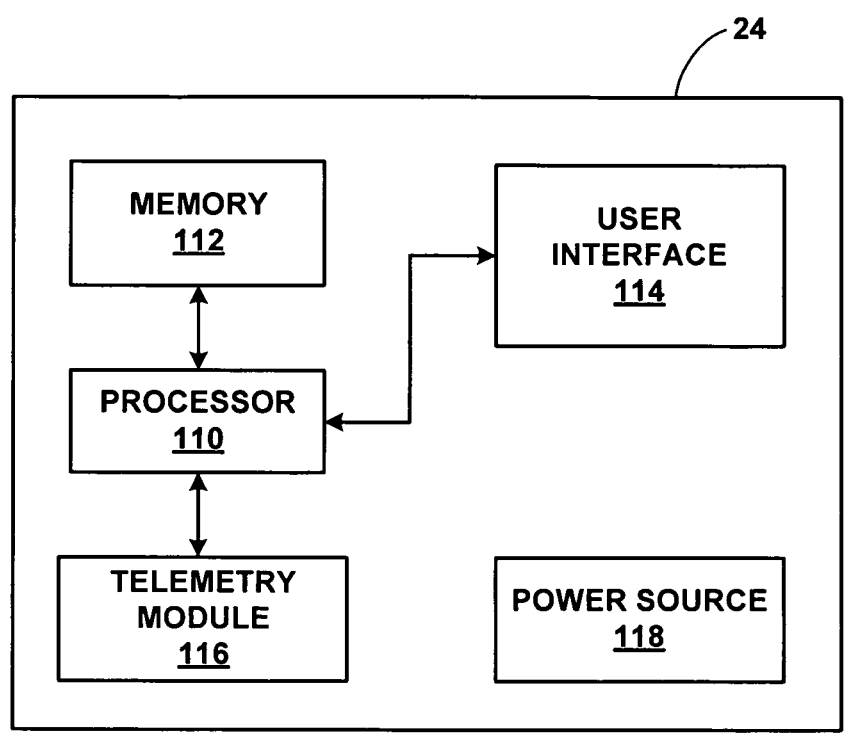
FIG. 6 is a functional block diagram illustrating an example configuration of an external programmer that facilitates user communication with the IMD.

FIG. 6 is functional block diagram illustrating an example configuration of programmer 24. As shown in FIG. 6, programmer 24 may include a processor 110, memory 112, user interface 114, telemetry module 116, and power source 118. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, modify therapy programs through individual or global adjustments or transmit the new programs to a medical device, such as IMD 16 (FIG. 1). The clinician may interact with programmer 24 via user interface 114, which may include display to present graphical user interface to a user, and a keypad or another mechanism for receiving input from a user.

The user may define maximum and minimum amplitude limits for EGM signals or other saturation parameters 81 within IMD 16 that processor 80 uses to detect when the EGM signal is saturation. The user may also use programmer 24 to adjust or control the integrity testing performed by IMD 16. For example, the user may use programmer 24 to program the number of test pulses, the timing of test pulses, the parameters of each test pulse, or any other aspects of the impedance measurements of lead integrity tests. In this manner, the user may be able to finely tune the integrity test to the specific condition of patient 14.

In addition, the user may receive an alert from IMD 16 indicating a potential integrity issue with the current sensing configuration via programmer 24. The user may respond to IMD 16 by selecting an alternative sensing configuration via programmer 24 or overriding the integrity issue if a cardiac event is occurring. Alternatively, IMD 16 may automatically select an alternative sensing configuration. Programmer 24 may prompt the user to confirm the selection of the alternative sensing configuration.

Processor 110 can take the form one or more microprocessors, DSPs, ASICs, FPGAs, programmable logic circuitry, or the like, and the functions attributed to processor 110 herein may be embodied as hardware, firmware, software or any combination thereof. Memory 112 may store instructions that cause processor 110 to provide the functionality ascribed to programmer 24 herein, and information used by processor 110 to provide the functionality ascribed to programmer 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before programmer 24 is used to program therapy for another patient.

Programmer 24 may communicate wirelessly with IMD 16, such as using RF communication or proximal inductive interaction. This wireless communication is possible through the use of telemetry module 116, which may be coupled to an internal antenna or an external antenna. An external antenna that is coupled to programmer 24 may correspond to the programming head that may be placed over heart 12, as described above with reference to FIG. 1. Telemetry module 116 may be similar to telemetry module 88 of IMD 16 (FIG. 4).

Telemetry module 116 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 110 of programmer 24 and/or one or more processors of one or more networked computers may perform all or a portion of the techniques described herein with respect to processor 80 and IMD 16. For example, processor 110 or another processor may receive, from IMD 16, a saturation indication from a narrow band channel 102, a clamp indication from a clamp circuit 109, or a digitized EGM signal via telemetry module 116. Processor 110 may determine whether an EGM signal is saturated using any of the techniques described above. Processor 110 or another processor may receive voltages or currents measured by IMD 16 to calculate impedance measurements, or may receive impedance measurements from IMD 16. Processor 110 or another processor may compare impedance measurements to evaluate lead integrity using any of the techniques described herein. Processor 110 or another processor may also control IMD 16 to switch sensing or therapy configurations, or may provide an alert, based on the evaluation or detection of the saturation of the signal, according to any of the techniques described herein. Processor 110 may store an EGM and marker channel at the time the signal was saturated in memory 112, e.g., for presentation with an alert.

Power source 118 delivers operating power to the components of programmer 24. Power source 118 may include a battery and a power generation circuit to produce the operating power. In some embodiments, the battery may be rechargeable to allow extended operation. Recharging may be accomplished by electrically coupling power source 118 to a cradle or plug that is connected to an alternating current (AC) outlet. In addition or alternatively, recharging may be accomplished through proximal inductive interaction between an external charger and an inductive charging coil within programmer 24. In other embodiments, traditional batteries (e.g., nickel cadmium or lithium ion batteries) may be used. In addition, programmer 24 may be directly coupled to an alternating current outlet to power programmer 24. Power source 118 may include circuitry to monitor power remaining within a battery. In this manner, user interface 114 may provide a current battery level indicator or low battery level indicator when the battery needs to be replaced or recharged. In some cases, power source 118 may be capable of estimating the remaining time of operation using the current battery.

Figure 7:
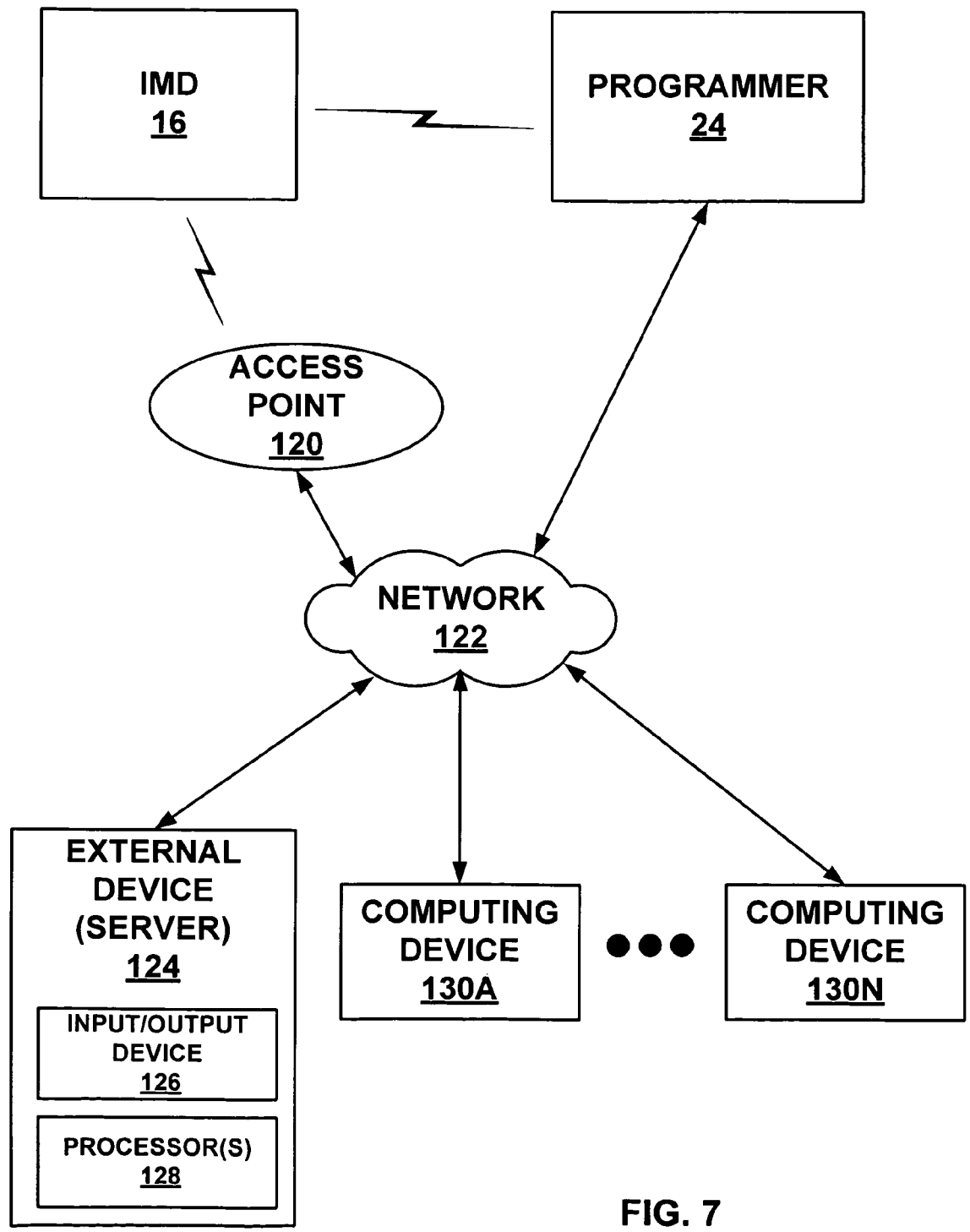
FIG. 7 is a block diagram illustrating an example system that includes an external device, such as a server, and one or more computing devices that are coupled to the IMD and programmer shown in FIG. 1 via a network.

FIG. 7 is a block diagram illustrating an example system that includes an external device, such as a server 124, and one or more computing devices 130A-130N, that are coupled to the IMD 16 and programmer 24 shown in FIG. 1 via a network 122. In this example, IMD 16 may use its telemetry module 88 to communicate with programmer 24 via a first wireless connection, and to communication with an access point 120 via a second wireless connection. In the example of FIG. 7, access point 120, programmer 24, server 124, and computing devices 130A-130N are interconnected, and able to communicate with each other, through network 122. In some cases, one or more of access point 120, programmer 24, server 124, and computing devices 130A-130N may be coupled to network 122 through one or more wireless connections. IMD 16, programmer 24, server 124, and computing devices 130A-130N may each comprise one or more processors, such as one or more microprocessors, DSPs, ASICs, FPGAs, programmable logic circuitry, or the like, that may perform various functions and operations, such as those described herein.

Access point 120 may comprise a device that connects to network 122 via any of a variety of connections, such as telephone dial-up, digital subscriber line (DSL), or cable modem connections. In other embodiments, access point 120 may be coupled to network 122 through different forms of connections, including wired or wireless connections. In some embodiments, access point 120 may be co-located with patient 14 and may comprise one or more programming units and/or computing devices (e.g., one or more monitoring units) that may perform various functions and operations described herein. For example, access point 120 may include a home-monitoring unit that is co-located with patient 14 and that may monitor the activity of IMD 16.

In some examples, server 124 or computing devices 130 may perform any of the various functions or operations described herein. As shown in FIG. 7, server 124 may include an input/output device 126 and processors 128, similar to programmer 24. A user may interact with server 124 via input/output device 126, similar to programmer 24. In addition, processors 128 may perform any calculations, data processing, communication relay, or any other task required to treat or monitor patient 14.

For example, server 124 or computing devices 130 may processor 110 or another processor may receive, from IMD 16, a saturation indication from a narrow band channel 102, a clamp indication from a clamp circuit 109, or a digitized EGM signal via network 122. Server 124 or computing devices 130 may determine whether an EGM signal is saturated using any of the techniques described above. Server 124 or computing devices 130 may receive voltages or currents measured by IMD 16 to calculate impedance measurements, or may receive impedance measurements from IMD 16 via network 122. Server 124 or computing devices 130 may compare impedance measurements to evaluate lead integrity using any of the techniques described herein. Server 124 or computing devices 130 may also control IMD 16 to switch sensing or therapy configurations, or may provide an alert, based on the evaluation or the detection of saturation, according to any of the techniques described herein. In some examples, server 124 may provide some or all of this functionality, and provide alerts to interested users, e.g., a physician for patient 14 or technician for a manufacturer of IMD 16 or leads 18, 20 and 22, via network 122 and computing devices 130.

In some cases, server 124 may be configured to provide a secure storage site for archival of sensing integrity information, such as impedance measurements and EGM signal saturation information, e.g., an EGM and/or marker channel illustrating the saturated signal, that has been collected from IMD 16 and/or programmer 24. Network 122 may comprise a local area network, wide area network, or global network, such as the Internet. In some cases, programmer 24 or server 124 may assemble sensing integrity information in web pages or other documents for viewing by and trained professionals, such as clinicians, via viewing terminals associated with computing devices 130A-130N. The system of FIG. 7 may be implemented, in some aspects, with general network technology and functionality similar to that provided by the Medtronic CareLink® Network developed by Medtronic, Inc., of Minneapolis, Minn.

Figure 8:
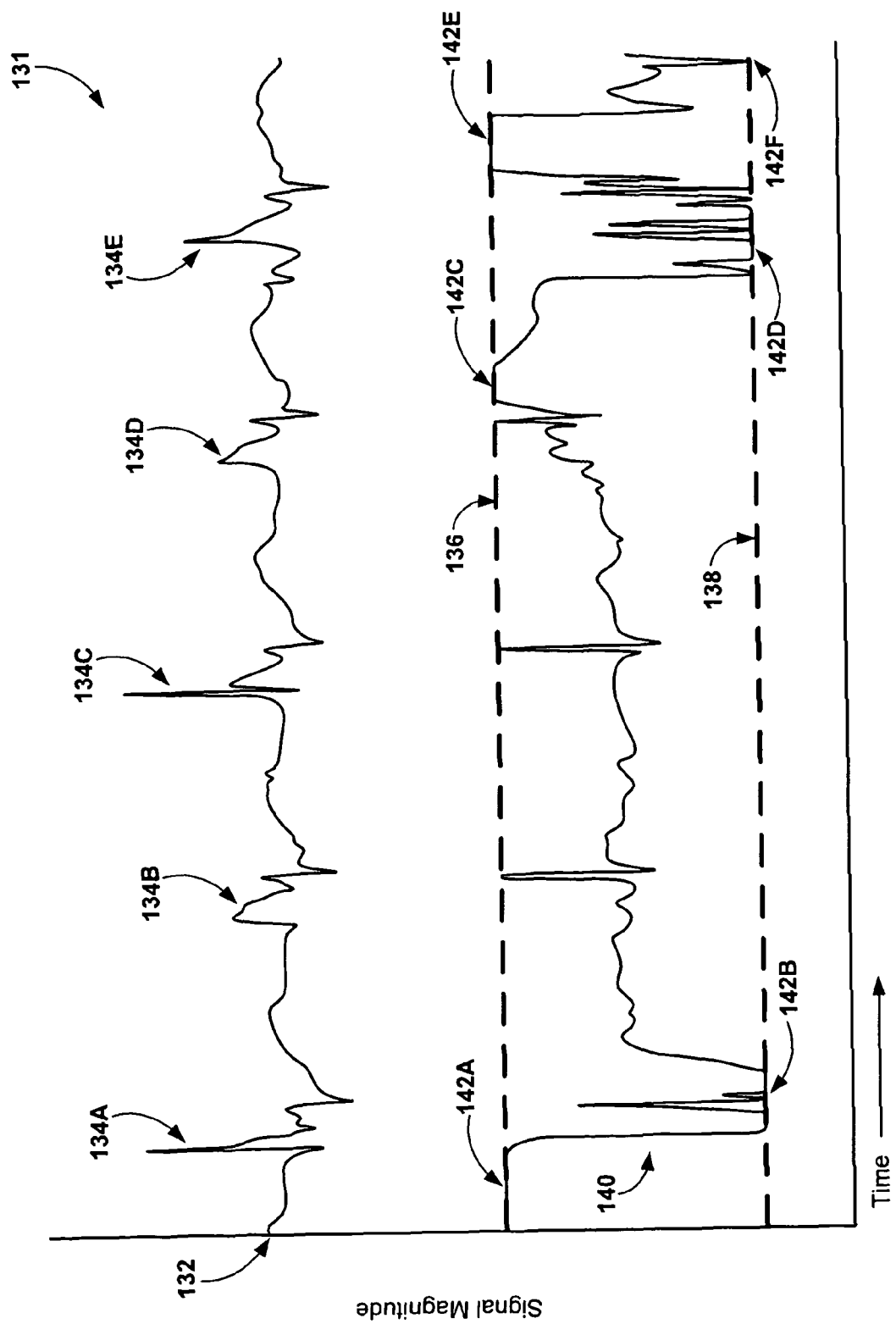
FIG. 8 is a graph illustrating an example of saturation of a cardiac electrogram (EGM) signal due to incomplete lead pin insertion into the IMD of FIG. 1.

FIG. 8 is a graph illustrating example of saturation of a cardiac electrogram (EGM) signal due to incomplete lead pin insertion into IMD 16 of FIG. 1. As shown in FIG. 8, graph 131 presents far-field EGM signal 132 and near-field EGM signal 140. Far-field EGM signal 132 is an example EGM signal of heart 12 from two electrodes spaced relatively far apart within patient 14. One of the electrodes of the sensing configuration is near or within heart 12 while another electrode for the sensing configuration is outside of the heart, e.g., electrode 58 of IMD 16. EGM signal 132 indicates the overall heart 12 function and shows cardiac events 134A, 134B, 134C, 134D, and 134E (collectively "cardiac events 134"). Cardiac events 134 may correspond to R-waves produced by the contraction of the right and left ventricles of heart 12, or other electrical signals produced during one heart cycle.

Both far-field EGM signal 132 and near-field EGM signal 140 may be produced with either narrow band channel 102 or wide band channel 104 of sensing module 86. In some cases, far-field EGM signal 132 may be produced by wide band channel 104 and narrow-field EGM signal 140 may be produced by narrow band channel 102, or vice versa. In any case, sensing module 86 employs a circuit that is configured to produce an EGM signal from the intrinsic electrical signals produced by heart 12.

Near-field EGM signal 140 is an example signal of heart 12 produced from a sensing configuration in or near heart 12, e.g., electrodes 40 and 42, correlated in time with signal 132. EGM signal 140 is saturated at multiple times within graph 131. Saturation events 142A, 142B, 142C, 142D, 142E, and 142F (collectively "saturation events 142") occur when EGM signal 140 reaches maximum amplitude limit 136 and minimum amplitude limit 138. During each of saturation events 142, EGM signal 140 is beyond the amplitude that IMD 16 can measure, which IMD 16 may interpret as a cardiac event, e.g., tachycardia, that requires a responsive therapeutic shock. However, saturation events 142 are actually caused by incomplete lead pin insertion from one of leads 18, 20, or 22 to connector block 34.

Incomplete lead pin insertion may cause intermittent breaks in the sensing circuit which manifests as saturation events 142, but other causes may also produce similar saturation events 142. Saturation events 142 may trigger impedance measurements to determine if there are breaks in the sensing circuit that are causing saturation events 142. In some cases, periodic lead integrity tests may not be able to detect the incomplete lead pin insertion because of the patient 14 position, or because the lead pin was once inserted completely. Therefore, integrity testing when saturation events 142 are detected may be able to detect intermittent or newly manifested integrity issues.

Maximum amplitude limit 136 and minimum amplitude limit 138 may be set depending upon the configuration of the circuit used to produce EGM signal 140. These thresholds may be set by an operational limit of the sensing channel, e.g., amplifier, or defined to set a desired range for the EGM signal 140. For example, maximum amplitude limit 136 may be set at +8 millivolts (mV) and minimum amplitude limit 128 may be set at −8 mV, for a signal range of 16 mV. As another example, maximum amplitude limit 136 may be set at +5 millivolts (mV) and minimum amplitude limit 128 may be set at −5 mV, for a signal range of 10 mV, while the operational limit of the sensing channel, e.g., the amplifier, is ±8 mV. Thus, the saturation thresholds need not be the same as an operational limit of a sensing or detection channel, and, as used herein with respect to the thresholds, the terms maximum and minimum do not denote absolute signal or operational maximums or minimums.

In some examples, the operational limit of the sensing channel may be set by clamp circuit 109. Generally, the signal range may be between 4 mV and 100 mV. More specifically, the signal range may be between 10 mV and 20 mV. Maximum amplitude limit 136 and minimum amplitude limit 138 may have differing positive and negative amplitudes to account for drift or EGM signals having predominantly positive or negative values. In addition, limits 136 and 138 may be changed during therapy by a clinician via programmer 24 or processor 80 of IMD 16.

In some examples, the EGM signal may only be considered saturated when the EGM signal meets either maximum amplitude limit 136 or minimum amplitude limit 138 for a saturation duration. The saturation duration may be used to prevent triggering lead integrity testing for any spike in EGM signal shorter than the saturation duration not indicative of integrity issues. In general, the saturation duration may be between 10 milliseconds (ms) and 1000 ms. More specifically, the saturation duration may be between 50 ms and 150 ms. The saturation duration may by satisfied when an EGM signal 140 meets either or both of maximum amplitude limit 136 and minimum amplitude limit 138 during the saturation duration, e.g. during signal "railing" between the maximum and minimum.

Processor 80 may determine when the saturation duration is exceeded by determining that the saturation event occurs for at least the saturation duration. Alternatively, processor 80 may determine that the saturation duration is exceeded by detecting saturation of EGM signal 140 for a certain number of consecutive samples. For example, processor 80 may detect saturation by sampling EGM signal 140 every 8 ms for ten consecutive samples. Alternatively, processor 80 may only require a certain percentage of samples within the saturation duration to meet either maximum amplitude limit 136 or minimum amplitude limit 138. In this case, saturation event 142F may not satisfy the saturation duration to trigger an impedance measurement.

In some cases, processor 80 may conduct multiple lead integrity tests after saturation of EGM signal 140 is detected. For example, processor 80 may conduct a second integrity test approximately 100 ms after the first integrity test as a confirmation of the first integrity test, e.g., impedance measurements. Additional confirmation integrity tests may be routinely performed or performed in response to the results of the impedance measurements. Alternatively, processor 80 may limit the number of lead impedance measurements, or frequency of measurements, to prevent continued impedance measurements during EGM signal saturation. For example, after performing a lead integrity test triggered from EGM signal saturation, processor 80 may not perform another lead integrity test for at least 5 minutes. This integrity test lockout period may be generally between 1 second and 60 minutes. More specifically, the integrity test lockout period may be between 1 minute and 10 minutes.

Figure 9:
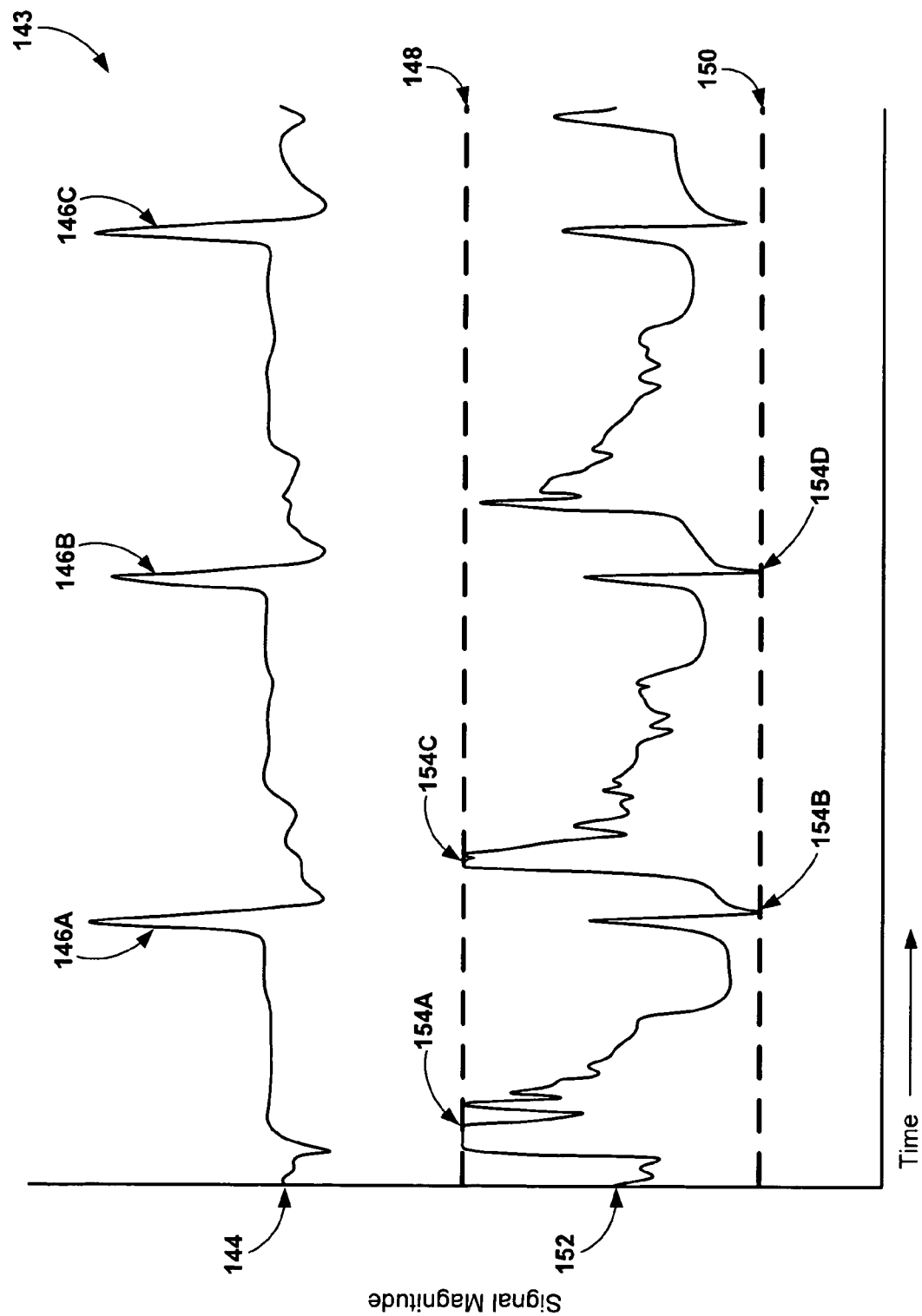
FIG. 9 is a graph illustrating an example of saturation of a cardiac EGM signal due to a conductor fracture of one of the implantable medical leads of FIG. 1.

FIG. 9 is a graph illustrating example of saturation of a cardiac (EGM) signals due to a conductor fracture of one of the implantable medical leads of FIG. 1. As shown in FIG. 9, graph 143 presents far-field EGM signal 144 and near-field EGM signal 152, similar to signals 132 and 140 of FIG. 8. Far-field EGM signal 144 is an example EGM signal of heart 12 from two electrodes spaced far apart within patient 14. EGM signal 144 indicates the overall heart 12 function and shows cardiac events 146A, 146B, and 146C (collectively "cardiac events 146"). Cardiac events 146 may correspond to R-waves produced by the contraction of the right and left ventricles of heart 12, or other electrical signals produced during one heart cycle.

Both far-field EGM signal 144 and near-field EGM signal 152 may be produced with either narrow band channel 102 or wide band channel 104 of sensing module 86. In some cases, far-field EGM signal 144 may be produced by wide band channel 104 and narrow-field EGM signal 140 may be produced by narrow band channel 152, or vice versa. In any case, sensing module 86 employs a circuit that is configured to produce an EGM signal from the intrinsic electrical signals produced by heart 12.

Near-field EGM signal 140 is an example signal of heart 12 produced from a sensing configuration in or near heart 12. EGM signal 152 is saturated at multiple times within graph 131. Saturation events 154A, 154B, 154C, and 154D (collectively "saturation events 154") occur when EGM signal 152 reaches maximum amplitude limit 148 and minimum amplitude limit 150. During each of saturation events 142, EGM signal 140 is beyond the amplitude that IMD 16 can measure, which IMD 16 may interpret as an arrhythmia that requires a responsive therapeutic shock. However, saturation events 154 may actually be caused by a conductor fracture in one of leads 18, 20, or 22 causing the inconsistent electrical signal of EGM signal 152. As described above in FIG. 8, the thresholds of maximum amplitude limit 148 and minimum amplitude limit 150 may be set by the operational limits of the sensing or detection channel, set by clamp circuit 109, or defined to set a desired range for the EGM signal 140.

Conductor fractures may manifest as saturation events 154. It should also be noted that other causes may also produce similar saturation events 154. In some cases, periodic lead integrity tests may not be able to detect the conductor fractures because they may be intermittent due to, for example, the position of patient 14. In addition, conductor fractures may occur at any time after the last lead integrity test. Therefore, integrity testing when saturation events 154 are detected may be able to detect intermittent integrity issues. As discussed above, processor 80 may determine when the saturation duration is exceeded by determining that the saturation event occurs for at least the saturation duration. Alternatively, processor 80 may determine that the saturation duration is exceeded by detecting saturation of EGM signal 140 for a certain number of consecutive samples.

Figure 10:
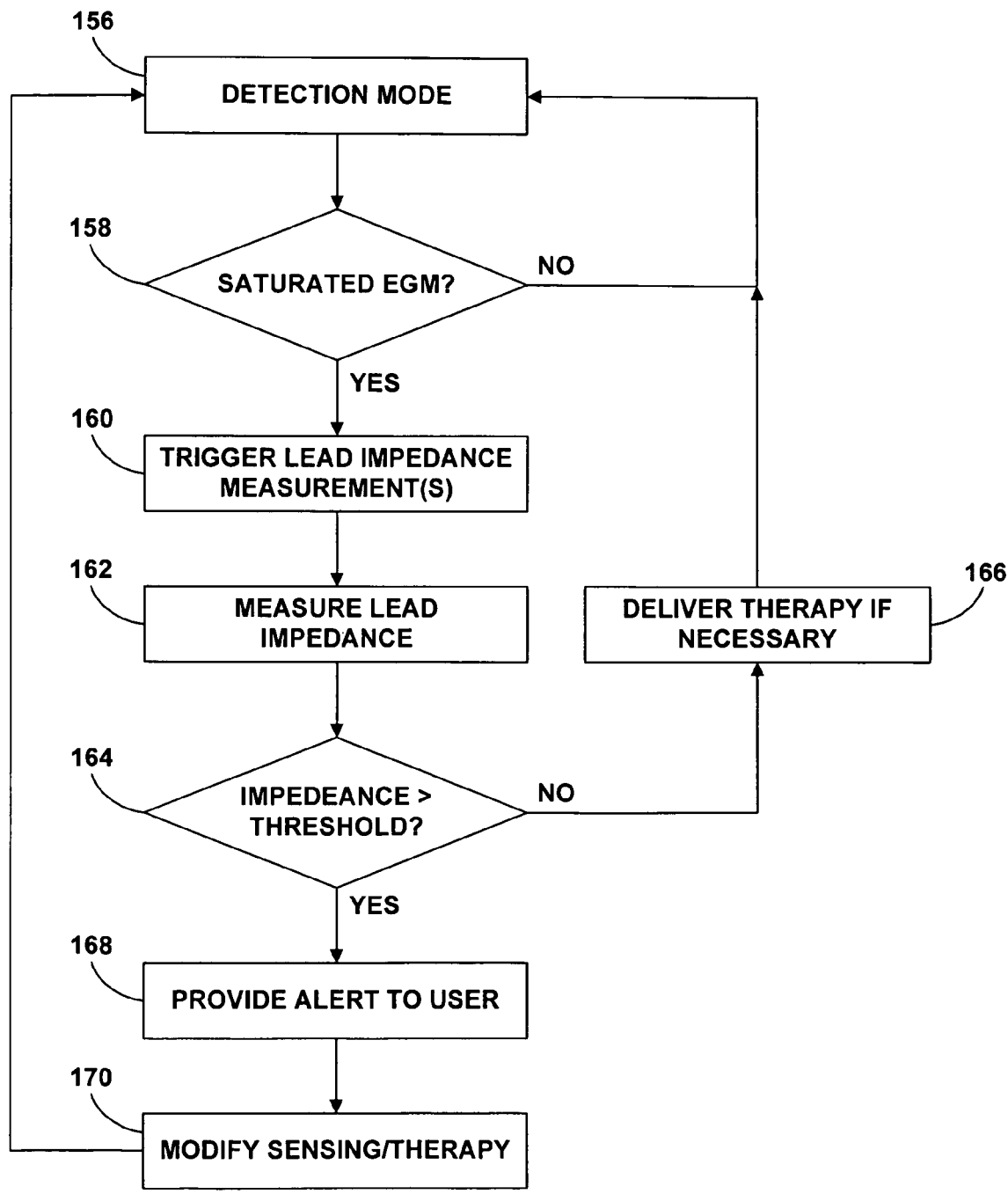
FIG. 10 is a flow diagram illustrating an example method for triggering a lead integrity test in response to saturation of the EGM signal.

FIG. 10 is a flow diagram illustrating an example method for triggering a lead integrity test in response to saturation of an EGM signal. As shown in FIG. 10, IMD 16 operates in a normal detection mode to identify any cardiac events that require therapy (156). If processor 80 does not detect a saturated EGM signal (158), processor 80 continues in normal detection mode (156). If processor 80 detects that the EGM signal is saturated (158), e.g., for a threshold saturation duration, using any of the techniques described herein, then processor 80 triggers lead impedance measurements for one or more electrical paths, including the sensing configuration that produced that saturated EGM (160). In some examples, processor 80 may trigger impedance measurements for all leads coupled to IMD 16, e.g., all electrical paths available to IMD 16, upon the detection of a saturated EGM signal. In some examples, instead of or in addition to triggering impedance measurements, processor 80 may store an EGM and/or marker channel illustrating the saturation in memory 82, or provide an alert, in response to detecting saturation of the EGM signal.

Once triggered, processor 80 and impedance measurement module 92 measure the impedances (162). If any of the impedances are greater than an impedance threshold stored in integrity test parameters 83 (164), processor 80 may determine that there is a lead-related condition, and may provide an alert to a user, e.g., via programmer 24 (168). Processor 80 may also modify a sensing or therapy configuration (170) before continuing in the detection mode (156). If the impedances are less than the impedance threshold (164), processor 80 may continue to deliver a responsive therapeutic shock if necessary (166) and continue the detection mode (156). As discussed above, the impedance threshold may be a predetermined, e.g., user-programmed, value, or a value determined based on previous impedance measurements, such as periodic impedance measurements. In some examples, the measured impedance compared to the threshold is an average or median of a number of measured impedances.

In some examples, processor 80 may take additional actions if any impedances are greater than the impedance threshold. Processor 80 may perform an additional confirmation lead impedance test of any electrical path. Alternatively, or additionally, processor 80 may select an alternative sensing configuration that does not have a lead-related condition. In addition, processor 80 may perform further tests if none of the impedances are greater than the impedance threshold (164). For example, processor 80 may examine the amplifier settings of either narrow band channel 102 or wide band channel 104 to determine if the amplifier settings specify too small of a range, e.g., for a particular patients physiological signals. Processor 80 may only deliver therapy if further tests also indicate that there are no lead-related conditions.

Various examples have been described. These and other examples are within the scope of the following claims. For example, although lead integrity testing in response to EGM saturation is directed herein toward cardiac therapy, this disclosure may also be applicable to other therapies in which lead integrity testing in response to detection of signal saturation may be appropriate. These therapies may include spinal cord stimulation, deep brain stimulation, pelvic floor stimulation, gastric stimulation, occipital stimulation, functional electrical stimulation, and any other stimulation therapy utilizing electrode sensing methods.

In addition, it should be noted that therapy system 10 may not be limited to treatment of a human patient. In alternative examples, therapy system 10 may be implemented in non-human patients, e.g., primates, canines, equines, pigs, and felines. These other animals may undergo clinical or research therapies that my benefit from the subject matter of this disclosure.

The techniques described in this disclosure, including those attributed to IMD 16, programmer 24, or various constituent components, may be implemented, at least in part, in hardware, software, firmware or any combination thereof. For example, various aspects of the techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic data storage media, optical data storage media, or the like. The instructions may be executed to support one or more aspects of the functionality described in this disclosure.

The invention claimed is:

1. A system comprising:
an implantable medical lead comprising one or more electrodes; an implantable medical device (IMD) coupled to the lead that senses a physiological signal of a patient via the electrodes; and a processor that configured to:
detect saturation of the signal; and
control the IMD to perform a lead impedance measurement of the implantable medical lead in response to the detection;
wherein the processor is configured to determine whether the signal is saturated for at least one of a threshold duration or a threshold number of samples, and controls the IMD to perform the lead integrity test in response to the determination.

2. A system comprising:
an implantable medical lead comprising one or more electrodes; an implantable medical device (IMD) coupled to the lead that senses a physiological signal of a patient via the electrodes; and a processor that configured to:
detect saturation of the signal; and
control the IMD to perform a lead impedance measurement of the implantable medical lead in response to the detection;
wherein the IMD comprises a clamp circuit that clamps the signal and provides an indication when the signal is clamped, and
wherein the processor is configured to detect saturation of the signal based on the indication.

* * * * *